(12) United States Patent
Aman et al.

(10) Patent No.: US 9,474,884 B2
(45) Date of Patent: Oct. 25, 2016

(54) BUMPED DILATOR TIP

(71) Applicants: Michael Aman, Sinking Spring, PA (US); Daniel Weinlick, Chesterbrook, PA (US)

(72) Inventors: Michael Aman, Sinking Spring, PA (US); Daniel Weinlick, Chesterbrook, PA (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 58 days.

(21) Appl. No.: 13/685,156

(22) Filed: Nov. 26, 2012

(65) Prior Publication Data

US 2014/0148651 A1 May 29, 2014

Related U.S. Application Data

(60) Provisional application No. 61/586,649, filed on Jan. 13, 2012.

(51) Int. Cl.
  *A61B 1/32* (2006.01)
  *A61M 29/00* (2006.01)
  *A61M 25/06* (2006.01)

(52) U.S. Cl.
  CPC ...... *A61M 29/00* (2013.01); *A61M 2025/0681* (2013.01); *Y10T 29/49826* (2015.01)

(58) Field of Classification Search
  CPC .............. A61B 17/34; A61B 17/3417; A61B 17/3421
  USPC .................................................. 600/203, 208
  See application file for complete search history.

(56) References Cited

U.S. PATENT DOCUMENTS

| | | | |
|---|---|---|---|
| 5,147,327 A | 9/1992 | Johnson | |
| 5,263,937 A | 11/1993 | Shipp | |
| 5,484,565 A | 1/1996 | Larsen et al. | |
| 5,618,272 A | 4/1997 | Nomura | |
| 5,922,443 A | 7/1999 | Larsen et al. | |
| 6,120,480 A | 9/2000 | Zhang et al. | |
| 6,436,119 B1 * | 8/2002 | Erb et al. ........... | 606/198 |
| 6,989,003 B2 | 1/2006 | Wing et al. | |
| 2010/0004730 A1 | 1/2010 | Benjamin et al. | |
| 2011/0028904 A1 | 2/2011 | Watanabe et al. | |
| 2013/0184736 A1 | 7/2013 | Aman et al. | |

FOREIGN PATENT DOCUMENTS

| | | |
|---|---|---|
| CA | 2197961 A1 | 8/1997 |
| CN | 2137939 Y | 7/1993 |
| CN | 201020142 Y | 2/2008 |
| CN | 101234047 A | 8/2008 |
| EP | 0514913 A2 | 11/1992 |
| JP | H0644553 U | 6/1994 |
| JP | 3020360 U | 1/1996 |
| JP | 09-225035 | 9/1997 |
| JP | 09322941 H | 12/1997 |
| WO | WO9730746 A1 | 8/1997 |

* cited by examiner

*Primary Examiner* — Andrew Yang
(74) *Attorney, Agent, or Firm* — Baker & Hostetler LLP

(57) ABSTRACT

The disclosure provides a dilator with a tip that has a bump, an assembly comprising the dilator and a sheath, and methods of use, where the bump on the tip is configured to reduce or minimize damage to the sheath, and to prevent trauma to a patient during insertion or removal.

20 Claims, 11 Drawing Sheets

BUMPED DILATOR TIP

Figure 1A:
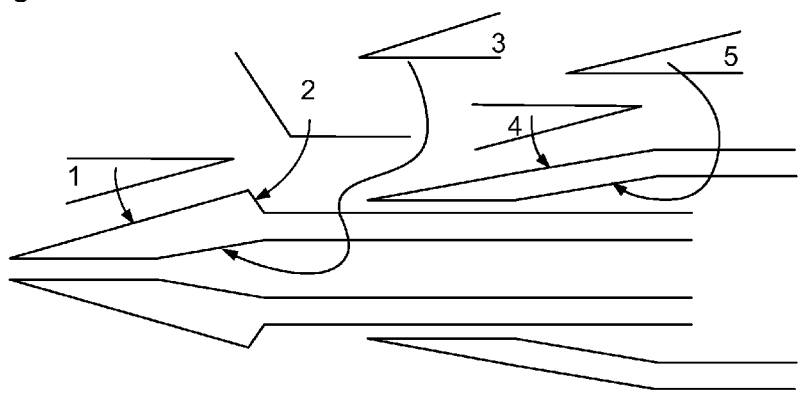

This application claims the full Paris Convention benefit of, and priority to U.S. Provisional Application No. 61/586,649, filed Jan. 13, 2012, entitled Novel Bumped Dilator Tip, which is incorporated herein by reference, as if fully set forth in its entirety.

FIELD OF THE DISCLOSURE

The disclosure relates to systems, methods, and devices for vascular access. In particular, the disclosure relates to dilators and sheaths, and assemblies thereof, as well as to related medical devices such as catheters, cannulae, introducers, trocars, dilation instruments, guide wires, rapid exchange systems, hubs, couplers, and valves, as well as known and any later developed emplacement apparatus and methods.

BACKGROUND OF THE DISCLOSURE

In medical practice, the introduction of drugs or instruments into a patient sometimes involves a device known as a dilator sheath assembly. The dilator and sheath each resemble a tube, where the dilator fits into the sheath, and where a narrow distal tip of the dilator (dilator tip) helps to introduce the wider sheath into the patient.

In some embodiments, the combination of dilator and sheath includes a transition region, where the generally narrower dilator transitions to the somewhat wider sheath. Where a dilator sheath assembly is inserted into a patient, the force of insertion can result in damage to the sheath, where damage occurs at the point of transition. The damaged medical instrument, in turn, can cause trauma to the patient, during continued insertion or during removal of the sheath from the patient. In other words, trauma can occur to tissue where insertion of the dilator-sheath assembly results in deformation (damage) of the sheath tip, where continued attempts to insert or withdraw the damaged sheath can traumatize the tissue.

During insertion into the body of a 2-part medical device assembly such as: sheath/dilator; trocar/dilator; sheath or catheter and needle; the transition from the primary insertion device (dilator or needle) to the secondary device (sheath, trocar, or catheter) creates a potential for resistance to insertion. No matter how small the radius or acute the lead angle of the distal tip of the sheath, catheter, or trocar, the transition can result in resistance and snagging as it progresses through the tissue and vessel wall.

Furthermore, attempts to improve insertion by making the distal taper of the sheath thinner have led to buckling or deforming of the sheath tip during insertion. Techniques for measuring sheath buckling or kinking are available (see, e.g., Monga, et al. (2004) Systematic evaluation of ureteral access sheaths. Urology. 63:834-836). The bumped dilator of the present disclosure functions through pre-dilation of the tissue and vessel wall so that the transition at the distal sheath tip encounters less resistance upon insertion. Those skilled in the art readily understand that "dilator" as defined by "bumped dilator" in this application is coextensive with any leading distal edge of an emplacement apparatus known or later developed.

General details of the structure and methods of use of dilator sheath are as follows. A dilator is often used to aid in the insertion of the sheath. Dilators have a long tubular section, the outside diameter of which may be slightly smaller than the inside diameter of the sheath, where the smaller diameter allows the dilator to be inserted without undue friction, and to be pulled back out of the sheath.

Alternatively, body of dilator can have outside diameter that is greater than inside diameter of body of sheath (in non-assembled state), where in the assembled state, the body of the dilator and the body of the sheath are held elastically in continuous contact with each other (but where friction is not sufficient to prevent longitudinal movements of the dilator within the sheath). Dilators also may have a pointed tip on the distal end and a hollow longitudinal passageway running the entire length thereof. In practice, a dilator is inserted into the patient's body through the sheath and along the guide wire, where the guide wire allows the distal tip to extend into the incision hole in the patient's tissues, carefully enlarging the hole. The dilator is then removed along the guide wire prior to insertion of a catheter along the guide wire and into the sheath.

Dilators comprise a dilator tip located at the distal end of the dilator. The dilator tip can be described with reference to the longitudinal tubular body of the dilator, that is, to the region of the dilator occupying the greatest surface area and volume of the dilator. Typically, the longitudinal body of a dilator is parallel or non-tapered, and having a constant diameter. The dilator tip can consist of a tapered distal tip (see, e.g., U.S. Pat. No. 5,885,217 issued to Gisselberg and Hicks, U.S. Pat. No. 7,422,571 issued to Schweikert and Nardeo, and US 2009/0105652 of Beal and King). Each of the above patent documents is hereby incorporated by reference. The proximal portion of the dilator can also be conformed to increase in radius, not by way of a taper, but by way of an annular region that is perpendicular (90 degree angle) to the longitudinal body of the dilator (see, e.g., U.S. Pat. No. 5,499,975 issued Cope and Arnett). Moreover, the proximal portion of a dilator tip can increase in radius by way of an overhang or ratchet-shape, as shown, for example, in U.S. Pat. No. 5,292,311 issued to Cope. These patents are hereby incorporated by reference in their entirety.

Following insertion of the dilator-sheath assembly and removal of the dilator, the sheath body forms a conduit for inserting a catheter or other medical articles, as known to artisans.

Methods for inserting a catheter or sheath into a blood vessel involve the use of the Seldinger technique, which includes the initial step of inserting a needle into a patient's blood vessel. A guide wire is inserted through the needle and into the vessel. The needle is removed, and a dilator and sheath combination are then inserted over the guide wire. The dilator and sheath combination is then inserted a short distance through the tissue into the vessel. The combination of the needle, dilator, and sheath, can be advanced over the guide wire into the blood vessel. After this combination has been advanced, the dilator is removed. The catheter is then inserted through the sheath into the vessel to a desired location. The Seldinger technique, and variations thereof, and devices used to perform this technique, are described in Seldinger (1953) Acta Radiologica 39:368-376; U.S. Pat. No. 7,722,567 issued to Tal, U.S. Pat. No. 7,972,307 issued to Kraus, et al, and U.S. Pat. No. 7,938,806 issued to Fisher, et al, which are incorporated by reference. U.S. Pat. No. 6,004,301 issued to Carter, incorporated by reference in its entirety, provides several elementary diagrams that disclose the insertion of a needle through the patient's flesh, with insertion into a blood vessel. Trauma, insult, and injury, are often issues that require management and longer hospital time. Likewise, preventing trauma, insult, or injury, is important for these devices.

After the incision hole is sufficiently enlarged, the dilator is removed, leaving the sheath and guide wire in position inserted into the incision hole. The catheter is then inserted into the sheath, through the incision hole and into the blood vessel, and the sheath is then removed from around the exterior of the catheter. The disclosure also contemplates embodiments comprising a solid dilator, that is, a dilator that does not comprise a lumen, as well as trocars, catheter-sheath devices, and other devices that access body lumens.

When removing the sheath, and where a catheter or other device needs to remain within the sheath and needs to remain within the blood vessel, removal of the sheath is made possible by using a splittable sheath, sometimes called peelable or "tearaway."

The following concerns the situation where the dilator-sheath assembly has been inserted into patient's blood vessel or other cavity, where the dilator has been withdrawn, and the dilator has been replaced with a catheter or other instrument. The sheath that can be split away from the catheter as the sheath is being removed from the patient. By splitting the sheath along its longitudinal axis as the sheath is being removed from the patient, the practitioner can pull out the sheath in such a way that the sheath can be removed without interfering with any hubs, luer fittings, clamps, cuffs, accessories assembled to the catheter (U.S. Pat. No. 7,938,806 issued to Fisher, et al.). Removal of the sheath, with use of either peelaway sheath or non-peelaway sheath, where residence of catheter remains in a blood vessel, has the advantage of eliminating any obstruction of blood flow through the vessel, that is, obstruction caused by the presence of the sheath.

Where a sheath includes a hub, the hub serves as a handle (wings; tabs), and as a mating point for the insertion and locking of the dilator device. When the sheath needs to be split apart to be successfully withdrawn from the patient's body while leaving the catheter in place, the hub will also have to be split apart in order to clear the catheter. Sheath splitting is necessary, for example, where the catheter has any encumbrance, such as a hub on its proximal end (see, e.g., U.S. Pat. No. 7,422,571 issued to Schweikert and Nardeo, which is incorporated herein by reference).

After the dilator is removed, and before the catheter is inserted through the sheath, the sheath becomes an open conduit, allowing blood to spurt from the vessel through the sheath or allowing air to be aspirated into the vessel through the sheath, neither of which is desirable or permissible. The practitioner conventionally has had to place a thumb or finger over the proximal opening of the sheath to prevent blood loss and air embolism; however, this restricts the practitioner's hand movement, and is not a reliable method. Alternatively, the device can include a valve for preventing blood loss and air emboli. For example, a valve can be configured to automatically close and seal the opening as soon as the dilator is removed.

SUMMARY OF THE DISCLOSURE

Briefly stated, the disclosure provides a dilator with a tip that has a bump, an assembly comprising the dilator and a sheath, and methods of use, where the bump on the tip is configured to reduce or minimize damage to the sheath, and to prevent trauma to a patient during insertion or removal.

The present disclosure provides a dilator-sheath in combination comprising (structure numbers not provided): an elongate tubular sheath, wherein the sheath comprises a sheath body, a sheath proximal end, and a sheath distal tip or end, wherein the sheath body has an inner or lumenal radius and the distal sheath tip has an inner or lumenal radius, wherein the sheath proximal end comprises a sheath housing with an aperture; said dilator-sheath combination further comprising a dilator having an elongate dilator shaft including a proximal end and a distal tip, wherein the dilator has a dilator hub at its proximal end, wherein the distal tip of the dilator comprises a radially enlarged dilation member (dilator bump), wherein the dilator bump comprises a proximal taper that increases in radius when moving from the proximal to distal direction, and wherein dilator bump also comprises a distal taper that decreases radius when moving from the proximal to distal direction, where dilator-sheath has longitudinal axis, and radius is measurable from longitudinal axis, wherein the dilator bump has a maximal radius, as measurable at a point between the proximal taper and the distal taper, wherein the dilator bump is capable of being passed through the elongate tubular sheath.

Also provided, is the above dilator-sheath combination, wherein the sheath housing and the dilator hub are capable of being reversibly connected, coupled, or locked to each other.

Also embraced is the above dilator-sheath combination, wherein the dilator and sheath are in an assembled state, and wherein the dilator and sheath are coupled by way of the sheath housing and dilator hub, wherein said coupled dilator-sheath combination is configured so that the dilator bump is fully exposed and the dilator bump is disposed entirely distally to the distal tip of the sheath.

Further encompassed is the above dilator-sheath combination of, that further comprises a package or enclosure that contains said dilator and said sheath in a non-assembled state.

Moreover, what is also provided is the above dilator-sheath combination, wherein said dilator and said sheath are in an assembled state. Also embraced is the above dilator-sheath combination, wherein the proximal taper of said dilator bump has a point of minimal radius, said dilator-sheath combination in assembled state comprises a gap as measured longitudinally, wherein said gap has a gap length, wherein the gap occurs between a distal gap terminus and a proximal gap terminus, wherein said distal gap terminus is defined as the point of said point of minimal radius of dilator bump, and wherein said proximal gap terminus is defined as position of distal point of sheath tip. Also provided is the above dilator-sheath combination, wherein the gap length is stably maintained by contact or coupling between dilator hub and sheath housing.

What is also contemplated is the above dilator-sheath combination, wherein the gap length is: (a) about 0.05 centimeters, (b) at least 0.04 centimeters, or (c) 0.04-0.06 centimeters. Further encompassed is the above dilator-sheath combination, wherein the dilator bump comprises a distal angle, a longitudinal axis, an external distal surface, wherein the distal angle is measurable by comparing longitudinal axis to external distal surface of dilator bump, wherein the angle is one of about 0.03 degrees, about 0.07 degrees, or about 0.15 degrees. Or one of 0.02-0.04 degrees, 0.06-0.08 degrees, or 0.14-0.16 degrees, and the like. What is also provided is the above dilator-sheath combination of, wherein the dilator bump comprises a proximal internal angle, a longitudinal axis, an internal proximal surface, wherein the proximal internal angle is measurable by comparing longitudinal axis to internal proximal surface of dilator bump, wherein the angle is one of about 0.022 degrees, about 0.078 degrees, or about 0.089 degrees.

In assembled embodiments, what is also embraced is the above dilator-sheath combination, in assembled state, wherein the dilator bump has a maximal radius, wherein the sheath body has an outer radius, wherein the assembled dilator sheath defines a radially-extending distance that is a 100% shadow radial distance, wherein the dilator bump maximum radius can be defined in terms of said 100% shadow radial distance, and wherein the dilator bump maximum radius is the sum of dilator body outside diameter plus about 50% of shadow radial distance.

In another aspect, what is provided is the above dilator-sheath combination, in assembled state, wherein the dilator bump has a maximal radius, wherein the sheath body has an outer radius, wherein the assembled dilator sheath defines a distance that is a 100% shadow radial distance, wherein the dilator bump maximum radius can be defined in terms of said 100% shadow radial distance, and wherein the dilator bump maximum radius is the sum of dilator body outside diameter plus about 75% of shadow radial distance. In yet another aspect, what is provided is the above dilator-sheath combination, in assembled state, wherein the dilator bump has a maximal radius, wherein the sheath body has an outer radius, wherein the assembled dilator sheath defines a distance that is a 100% shadow radial distance, wherein the dilator bump maximum radius can be defined in terms of said 100% shadow radial distance, and wherein the dilator bump maximum radius is greater than the dilator body outside diameter, but does not exceed the sum of dilator body outside diameter plus 100% of shadow radial distance.

Moreover, what is encompassed is the above dilator-sheath combination, in assembled state, wherein the dilator bump has a maximal radius, wherein the sheath body has an outer radius, wherein the assembled dilator sheath defines a distance that is a 100% shadow radial distance, wherein the dilator bump maximum radius can be defined in terms of said 100% shadow radial distance, and wherein the dilator bump maximum radius is greater than the dilator body outside diameter, and exceeds the sum of dilator body outside diameter plus 100% of shadow radial distance.

In yet another embodiment, what is provided is the above dilator-sheath combination, wherein the sheath comprises a distal sheath tip diameter, and a sheath body diameter, wherein said distal sheath tip diameter is smaller than said sheath body diameter, when measured in non-assembled state.

Also provided, is the above dilator-sheath combination, wherein sheath of said dilator-sheath comprises a distal sheath tip diameter, and a sheath body diameter, wherein said distal sheath tip diameter is smaller than said sheath body diameter, when measured in assembled state. Also provided is the above dilator-sheath combination, wherein the sheath comprises a polytetramethylene glycol based polyurethane elastomer. In another embodiment, what is provided is the above dilator-sheath combination, wherein the dilator comprises a high density polyethylene (HDPE) resin. In another aspect, what is embraced is the above dilator-sheath combination, that is assembled, wherein in use the distal sheath tip is capable of being moved towards the dilator bump and to contact the proximal taper of the dilator bump during insertion of assembled dilator sheath combination into a patient, wherein the distal sheath tip is further capable of being moved over the dilator bump and to contact distal taper of dilator bump during insertion of assembled dilator sheath combination into said patient, wherein the distal sheath tip is capable of spontaneous movement, that reverses and eliminates contact with distal taper of dilator bump, and also substantially reverses and substantially eliminates contact with proximal taper of dilator bump, wherein said spontaneous movement that reverses contact of distal sheath tip with the dilator bump prevents damage to patient during withdrawal of the assembled dilator sheath combination from the patient.

In yet another embodiment, what is embraced is the above dilator-sheath combination, wherein terminus of sheath taper can contact terminus of dilator bump distal taper, and does not form a face-to-face configuration. Manufacturing embodiments are provided, that is, a method of manufacturing the above dilator-sheath combination, comprising inserting the dilator into the sheath, or comprising securing the dilator and the sheath into a package. Transferring embodiments are provided, that is, a method for transferring at least a portion of the dilator of the above assembled dilator-sheath combination to an interior part of a subject or patient, comprising contacting the distal tip of the dilator to a pre-formed hole or incision in the patient, and exerting a vector force to the dilator-sheath combination, wherein the vector force is in the same direction as the longitudinal axis of the dilator-sheath. Also provided is the above method, wherein in use at least a portion of the dilator enters a blood vessel. Also provided is the above method, further comprising transferring at least a portion of the sheath to an interior part of the subject or patient. In embodiments, the interior part comprises a blood vessel, the interior part does not comprise a blood vessel, the interior part comprises a urinary bladder, the interior part comprises a heart chamber, the interior part comprises an intestinal lumen.

The present disclosure provides a dilator-sheath in combination comprising (structure numbers provided): an elongate tubular sheath, wherein the sheath comprises a sheath body, a sheath proximal end, and a sheath distal tip or end, wherein the sheath body has an inner or lumenal radius and the distal sheath tip has an inner or lumenal radius, wherein the sheath proximal end comprises a sheath housing with an aperture; said dilator-sheath combination further comprising a dilator having an elongate dilator shaft including a proximal end and a distal tip, wherein the dilator has a dilator hub at its proximal end, wherein the distal tip of the dilator comprises a radially enlarged dilation member (dilator bump), wherein the dilator bump comprises a proximal taper that increases in radius when moving from the proximal to distal direction, and wherein dilator bump also comprises a distal taper that decreases radius when moving from the proximal to distal direction, where dilator-sheath has longitudinal axis, and radius is measurable from longitudinal axis, wherein the dilator bump has a maximal radius, as measurable at a point between the proximal taper and the distal taper, wherein the dilator bump is capable of being passed through the elongate tubular sheath.

Also provided, is the above dilator-sheath combination, wherein the sheath housing and the dilator hub are capable of being reversibly connected, coupled, or locked to each other.

Also embraced is the above dilator-sheath combination, wherein the dilator and sheath are in an assembled state, and wherein the dilator and sheath are coupled by way of the sheath housing and dilator hub, wherein said coupled dilator-sheath combination is configured so that the dilator bump is fully exposed and the dilator bump is disposed entirely distally to the distal tip of the sheath.

Further encompassed is the above dilator-sheath combination of, that further comprises a package or enclosure that contains said dilator and said sheath in a non-assembled state.

Moreover, what is also provided is the above dilator-sheath combination, wherein said dilator and said sheath are in an assembled state. Also embraced is the above dilator-sheath combination, wherein the proximal taper of said dilator bump has a point of minimal radius, said dilator-sheath combination in assembled state comprises a gap as measured longitudinally, wherein said gap has a gap length (28, 61), wherein the gap occurs between a distal gap terminus and a proximal gap terminus, wherein said distal gap terminus is defined as the point of said point of minimal radius of dilator bump, and wherein said proximal gap terminus is defined as position of distal point of sheath tip. Also provided is the above dilator-sheath combination, wherein the gap length is stably maintained by contact or coupling between dilator hub (78) and sheath housing (74).

What is also contemplated is the above dilator-sheath combination, wherein the gap length (28, 61) is: (a) about 0.05 centimeters, (b) at least 0.04 centimeters, or (c) 0.04-0.06 centimeters. Further encompassed is the above dilator-sheath combination, wherein the dilator bump comprises a distal angle (1, 31), a longitudinal axis, an external distal surface, wherein the distal angle is measurable by comparing longitudinal axis to external distal surface of dilator bump, wherein the angle is one of about 0.03 degrees, about 0.07 degrees, or about 0.15 degrees. Or one of 0.02-0.04 degrees, 0.06-0.08 degrees, or 0.14-0.16 degrees, and the like. What is also provided is the above dilator-sheath combination of, wherein the dilator bump comprises a proximal internal angle (3, 33), a longitudinal axis, an internal proximal surface, wherein the proximal internal angle is measurable by comparing longitudinal axis to internal proximal surface of dilator bump, wherein the angle is one of about 0.022 degrees, about 0.078 degrees, or about 0.089 degrees.

In assembled embodiments, what is also embraced is the above dilator-sheath combination, in assembled state, wherein the dilator bump has a maximal radius (86, 96), wherein the sheath body has an outer radius (23, 53), wherein the assembled dilator sheath defines a radially-extending distance that is a 100% shadow radial distance (200), wherein the dilator bump maximum radius can be defined in terms of said 100% shadow radial distance, and wherein the dilator bump maximum radius is the sum of dilator body outside diameter (20, 50) plus about 50% of shadow radial distance.

In another aspect, what is provided is the above dilator-sheath combination, in assembled state, wherein the dilator bump has a maximal radius (86, 96), wherein the sheath body has an outer radius (23, 53), wherein the assembled dilator sheath defines a distance that is a 100% shadow radial distance (200), wherein the dilator bump maximum radius can be defined in terms of said 100% shadow radial distance, wherein the dilator bump maximum radius is the sum of dilator body outside diameter (20, 50) plus about 75% of shadow radial distance.

In yet another aspect, what is provided is the above dilator-sheath combination, in assembled state, wherein the dilator bump has a maximal radius (86, 96), wherein the sheath body has an outer radius (23, 53), wherein the assembled dilator sheath defines a distance that is a 100% shadow radial distance (200), wherein the dilator bump maximum radius can be defined in terms of said 100% shadow radial distance, and wherein the dilator bump maximum radius is greater than the dilator body outside diameter (20, 50), but does not exceed the sum of dilator body outside diameter plus 100% of shadow radial distance.

Moreover, what is encompassed is the above dilator-sheath combination, in assembled state, wherein the dilator bump has a maximal radius (86, 96), wherein the sheath body has an outer radius (23, 53), wherein the assembled dilator sheath defines a distance that is a 100% shadow radial distance (200), wherein the dilator bump maximum radius can be defined in terms of said 100% shadow radial distance, and wherein the dilator bump maximum radius is greater than the dilator body outside diameter (20, 50), and exceeds the sum of dilator body outside diameter plus 100% of shadow radial distance.

In yet another embodiment, what is provided is the above dilator-sheath combination, wherein the sheath comprises a distal sheath tip diameter (21, 51), and a sheath body diameter (22, 52), wherein said distal sheath tip diameter is smaller than said sheath body diameter, when measured in non-assembled state.

Also provided, is the above dilator-sheath combination, wherein sheath of said dilator-sheath comprises a distal sheath tip diameter (21, 51), and a sheath body diameter (22, 52), wherein said distal sheath tip diameter is smaller than said sheath body diameter, when measured in assembled state. Also provided is the above dilator-sheath combination, wherein the sheath comprises a polytetramethylene glycol based polyurethane elastomer. In another embodiment, what is provided is the above dilator-sheath combination, wherein the dilator comprises a high density polyethylene (HDPE) resin. In another aspect, what is embraced is the above dilator-sheath combination, that is assembled, wherein in use the distal sheath tip is capable of being moved towards the dilator bump and to contact the proximal taper of the dilator bump during insertion of assembled dilator sheath combination into a patient, wherein the distal sheath tip is further capable of being moved over the dilator bump and to contact distal taper of dilator bump during insertion of assembled dilator sheath combination into said patient, wherein the distal sheath tip is capable of spontaneous movement, that reverses and eliminates contact with distal taper of dilator bump, and also substantially reverses and substantially eliminates contact with proximal taper of dilator bump, wherein said spontaneous movement that reverses contact of distal sheath tip with the dilator bump prevents damage to patient during withdrawal of the assembled dilator sheath combination from the patient.

In yet another embodiment, what is embraced is the above dilator-sheath combination, wherein terminus (61) of sheath taper can contact terminus (also 61) of dilator bump distal taper, and does not form a face-to-face configuration. Manufacturing embodiments are provided, that is, a method of manufacturing the above dilator-sheath combination, comprising inserting the dilator into the sheath, or comprising securing the dilator and the sheath into a package. Transferring embodiments are provided, that is, a method for transferring at least a portion of the dilator of the above assembled dilator-sheath combination to an interior part of a subject or patient, comprising contacting the distal tip of the dilator to a pre-formed hole or incision in the patient, and exerting a vector force to the dilator-sheath combination, wherein the vector force is in the same direction as the longitudinal axis of the dilator-sheath. Also provided is the above method, wherein in use at least a portion of the dilator enters a blood vessel. Also provided is the above method, further comprising transferring at least a portion of the sheath to an interior part of the subject or patient. In embodiments, the interior part comprises a blood vessel, the interior part does not comprise a blood vessel, the interior part comprises a urinary bladder, the interior part comprises a heart chamber, the interior part comprises an intestinal lumen.

In yet another aspect, the disclosure provides the above dilator-sheath combination, wherein the sheath comprises a polytetramethylene glycol based polyurethane elastomer, as well as the above dilator-sheath combination, wherein the dilator comprises a high density polyethylene (HDPE) resin. In exclusionary embodiments, the disclosure excludes sheath that does not comprise polytetramethylene glycol based polyurethane elastomer. In another exclusionary embodiment, the disclosure excludes dilator that does not comprise a high density polyethylene (HDPE) resin.

Furthermore, present disclosure encompasses the above dilator-sheath combination of, that is assembled, wherein in use the distal sheath tip is capable of being moved towards the dilator bump and to contact the proximal taper of the dilator bump during insertion of assembled dilator sheath combination into a patient, wherein the distal sheath tip is further capable of being moved over the dilator bump and to contact distal taper of dilator bump during insertion of assembled dilator sheath combination into said patient, wherein the distal sheath tip is capable of spontaneous movement, that reverses and eliminates contact with distal taper of dilator bump, and also substantially reverses and substantially eliminates contact with proximal taper of dilator bump, wherein said spontaneous movement that reverses contact of distal sheath tip with the dilator bump prevents damage to patient during withdrawal of the assembled dilator sheath combination from the patient.

In another aspect, the disclosure provides the above dilator-sheath combination, wherein terminus (61) of sheath taper can contact terminus (also 61) of dilator bump distal taper, and does not form a face-to-face configuration; as well as a method of manufacturing the above dilator-sheath combination, comprising inserting the dilator into the sheath, or comprising securing the dilator and the sheath into a package; as well as a method for transferring at least a portion of the sheath of the above assembled dilator-sheath combination to an interior part of a subject or patient, comprising contacting the distal tip of the dilator to a pre-formed hole or incision in the patient, and exerting a vector force to the dilator-sheath combination, wherein the vector force has a component that is in the same direction as the longitudinal axis of the dilator-sheath, and wherein the vector force is in the direction of the patient's skin.

According to embodiments, disclosure provides a dilation member (or dilator) and a sheath, where the sheath is more flexible relative to the dilation member (or dilator), wherein a portion of the dilation member that has a maximum diameter that is larger than at least a portion of the sheath inner diameter and outer diameter is capable of passing through the sheath by means of radial stretching of the sheath and negligible compression of the dilation member.

In embodiments, what is provided is a dilator-sheath assembly comprising in combination: an elongate tubular single layer sheath including proximal and distal ends, wherein the sheath comprises a sheath body and a sheath distal end, wherein the sheath body has an inner or lumenal radius and the distal sheath end has an inner or lumenal radius, wherein the radius of the distal sheath end is measured from the longitudinal axis to the inner or lumenal surface of the distal sheath end, and wherein the radius of the sheath body is measured from the longitudinal axis to the inner or lumenal surface of the sheath body, and wherein the distal sheath end radius and sheath body radius are measured with the dilator and sheath are in the non-assembled state; wherein the wherein the proximal end of the sheath comprises a housing with an aperture; a dilator having an elongate dilator shaft including proximal and distal ends, wherein the dilator has a hub at its proximal end, the dilator shaft extending though the aperture, through the housing and through the tubular sheath; the distal end of the dilator having a radially enlarged dilation member having a proximally extending taper and a substantially uniform distally extending taper; wherein the radially enlarged dilation member (dilator bump) has a maximal radius that is at least greater than 0.001 inch, at least greater than 0.002 inch, at least greater than 0.004 inch, at least greater than 0.005 inch, at least greater than 0.008 inch, at least greater than 0.010 inch, at least greater than 0.015 inch, at least greater than 0.020 inch, at least greater than 0.040 inch, and the like, beyond the radius of the distal sheath end, as measurable at any point at the distal sheath end, when the dilator and sheath are assembled together, wherein the enlarged dilation member is capable of preventing deformation or damage to the distal sheath end during insertion of the dilator-sheath assembly through a biological tissue, and where the dilator-sheath assembly is adapted to substantially prevent resistance between the biological tissue and the distal sheath end during said insertion of the dilator-sheath assembly, the sheath housing and the dilator hub being detachably connected to each other; and the sheath having a length such that when the housing and the hub are fully connected, the distal end of the sheath is disposed proximally of the proximally extending taper of the dilation member and distal end of the sheath is in contact with the dilator shaft.

In embodiments, what is also encompassed in the above dilator-sheath, wherein the configuration of dilation features disposed along the proximally tapered end enables ingress into a wound site without exceeding plastic deformation limits of the skin bordering the site, and whereby elastic deformation of said skin remains available for ingress to and egress from said site for other medical devices in that under tissue insult, injury, or trauma, during the same or different procedures.

Moreover, what is also encompassed is the above dilator-sheath, wherein the dilator comprises a dilator hub. What is also embraced is the above dilator-sheath, wherein the sheath comprises a sheath hub or sheath housing.

In another aspect, what is encompassed is the above dilator-sheath, wherein the dilator contains a dilator couple, wherein the sheath contains a sheath couple, wherein the dilator couple is configured for coupling to the sheath couple.

Furthermore, what is encompassed is the above dilator-sheath, wherein the coupling is mediated by at least one thread comprised by the dilator hub and at least one thread comprised by the sheath hub or housing. In yet another aspect, what is encompassed is the above dilator-sheath assembly, wherein the dilator hub does not comprise at least one thread, and the sheath hub does not comprise at least one thread.

Moreover, what is encompassed is the above dilator-sheath, wherein the sheath has an elasticity; wherein a distance of contact resides between the sheath tip and body of dilator in the assembled dilator-sheath; wherein the dilator bump has a maximal diameter; wherein the sheath has a tapered sheath tip that is has a greater diameter proximally and a narrow diameter distally; wherein the maximal diameter of the dilator bump is greater than each of the incremental progression of diameters over substantially the entire distal-to-proximal distance of the sheath tip; wherein said elasticity, distance of contact, and maximal diameter of the dilator bump relative to the progression of diameters of the tapered sheath tip, are configured to prevent deformation of the sheath tip, where said deformation substantially extends beyond the plastic limit of the sheath tip.

In another embodiment, what is provided is the above dilator-sheath assembly, further comprising a space that is proximal to the sheath tip resides between the inner (lumenal) surface of the sheath and the outer surface of the body of the dilator, in the assembled dilator-sheath, wherein said elasticity, distance of contact, maximal diameter of the dilator bump relative to the progression of diameters of the tapered sheath tip, and space, are configured to prevent deformation of the sheath tip, where said deformation substantially extends beyond the plastic limit of the sheath tip.

Additionally embraced is the above dilator-sheath, further comprising a lubricant, wherein said elasticity, distance of contact, maximal diameter of the dilator bump relative to the progression of diameters of the tapered sheath tip, and lubricant, are configured to prevent deformation of the sheath tip, where said deformation substantially extends beyond the plastic limit of the sheath tip.

Also encompassed is the above, dilator-sheath assembly, wherein said substantially extends beyond the plastic limit, is under 0.1% beyond the plastic limit, under 1.0% beyond the plastic limit, under 10% beyond the plastic limit, or under 50% beyond the plastic limit.

In other aspects, what is provided is a method for using the above dilator-sheath assembly, comprising inserting the dilator-sheath assembly through a tissue of a patient, a flesh of a patient, a thin polymer film, or an animal skin, and removing the dilator from the dilator-sheath assembly, and a method of manufacturing the above dilator-sheath assembly, comprising molding, casting, or shaping the dilator; and molding, casting, or forming the sheath.

BRIEF DESCRIPTIONS OF THE FIGURES

FIG. 1. A. Angles of assembly of dilator and sheath of dilator sheath assembly. B. Lengths and widths of assembly of dilator and sheath. C. Additional lengths and widths. D. Dimensions of test cylinder.

FIG. 2. Relative positions of sheath and dilator: A. Relative positions at intermediate points during insertion, as well as after completing insertion. B. Sheath tip abuts dilator bump. C. Sheath tip overriding dilator bump.

FIG. 3. A. Angles of assembly of dilator and sheath of rounded bump embodiment of dilator sheath assembly. B. Lengths and widths of assembly of dilator and sheath of rounded bump embodiment of dilator sheath assembly. C. Additional lengths and widths. D. Dimensions of test cylinder.

FIG. 4. Relative positions of sheath and dilator in rounded bump embodiment, which may occur during use or testing. A. Prior to insertion and after completing insertion. B. Sheath tip abuts dilator bump. C. Sheath tip overriding dilator bump.

Figure 5:
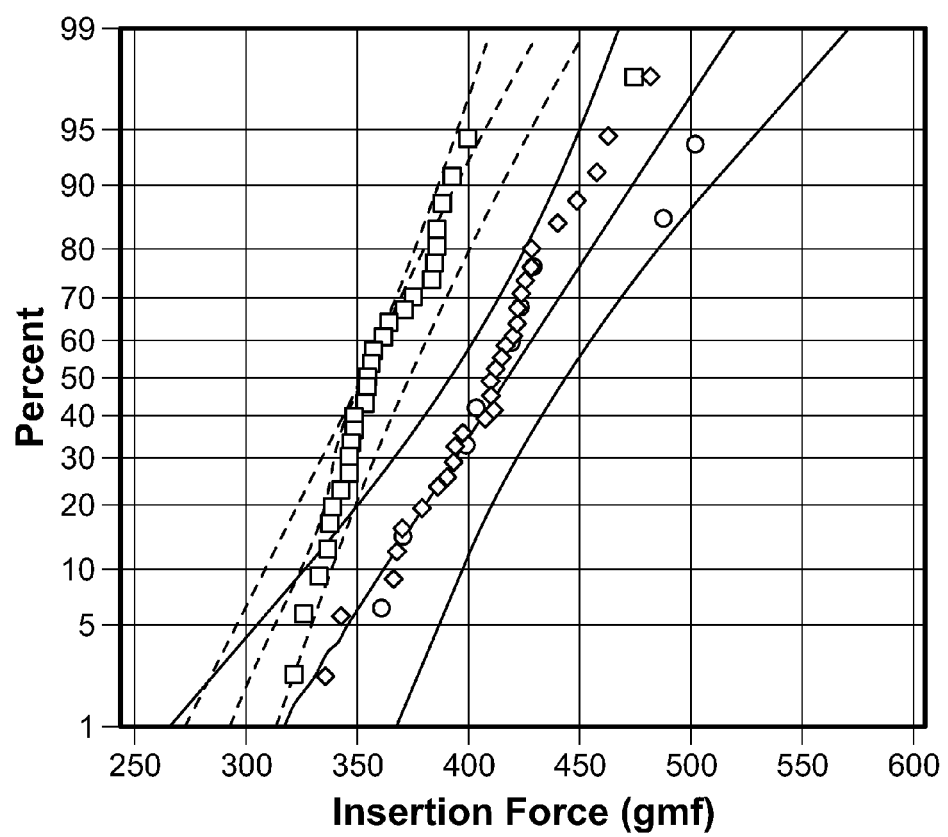

FIG. 5. Insertion of three embodiments into and through a thin polymer film.

Figure 6:
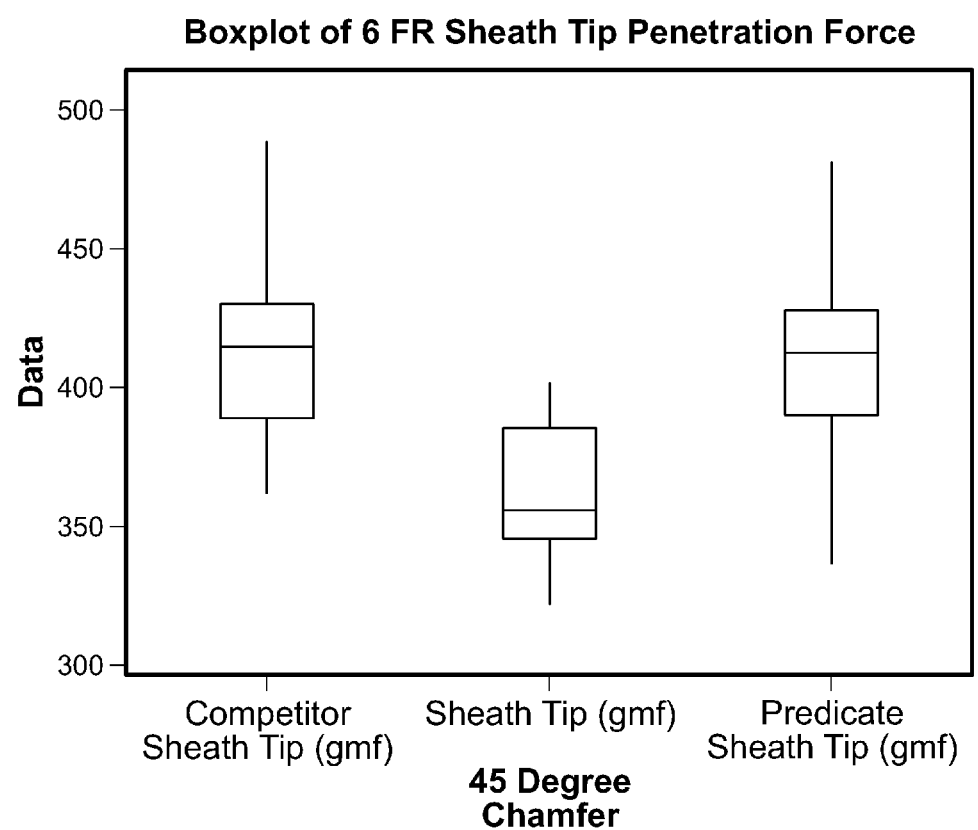

FIG. 6. Boxplot of sheath tip penetration test, showing data from insertion of three embodiments into and through a thin polymer film. To clarify, the data points given represent the force as the sheath tip penetrates the film.

Figure 7:
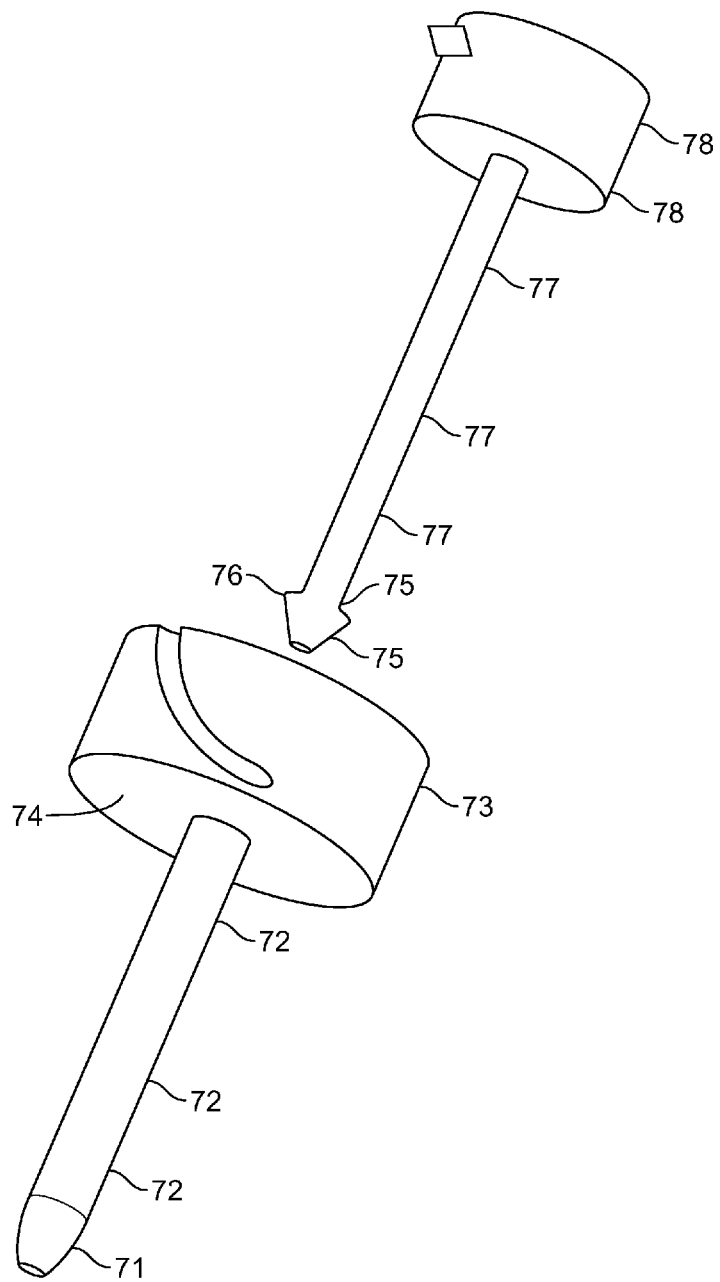

FIG. 7. Three dimensional drawing of dilator and sheath, in non-assembled state.

Figure 8A:
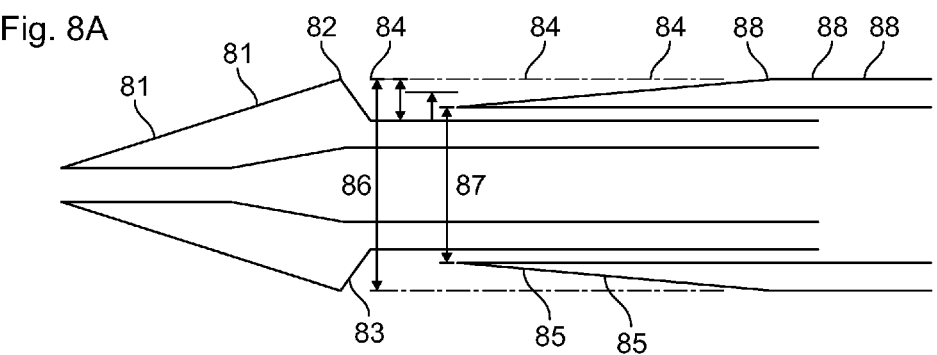
Figure 8B:
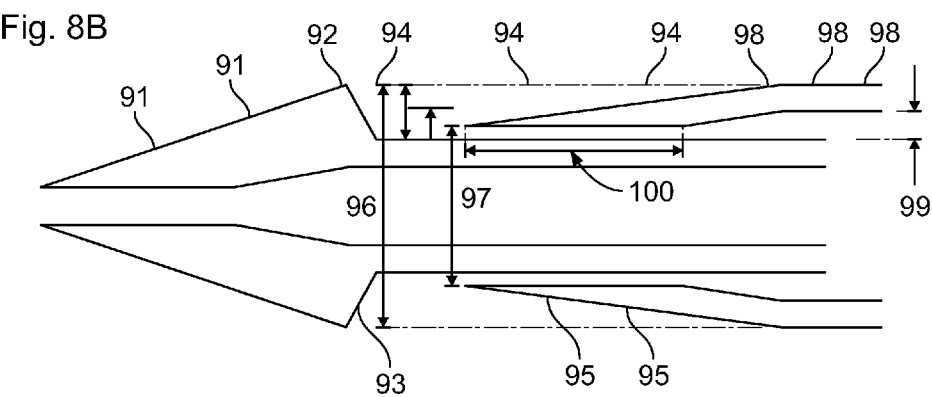
Figure 8C:
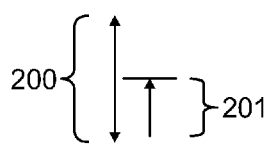

FIG. 8. Configuration of "shadow region" of dilator-sheath assembly. FIG. 8A shows shadow region, where interior diameter of sheath tip is same as interior diameter of body of sheath. FIG. 8B shows shadow region, where interior diameter of sheath tip contacts dilator, but interior diameter of sheath body, at least in non-assembled state, does not contact sheath body, or less firmly contacts sheath body. FIG. 8C is a legend, showing radial distance of sheath shadow, and 50% of radial distance of sheath shadow. The shadow is cast by an imaginary light that has a diameter equal to dilator bump, where the light is located at an infinite distance distal to dilator tip, where the light is centrally intersected by longitudinal axis of dilator sheath.

Figure 9A:
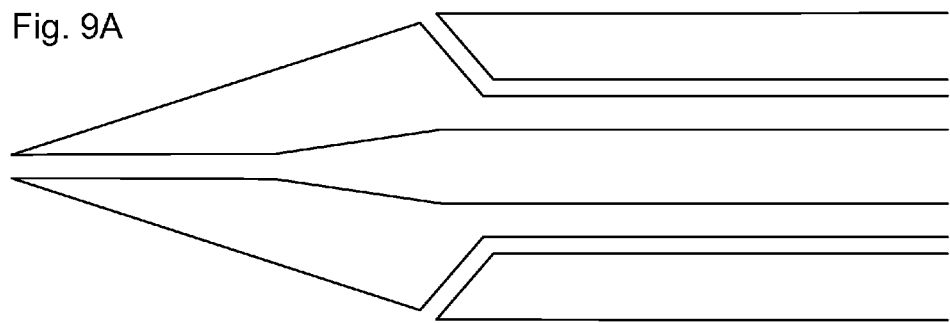

FIG. 9. Face-to-face configurations. FIGS. 9A, B, and C, disclose three non-limiting embodiments of the face-to-face configurations, that is, where sheath tip abuts proximal taper of dilator.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

DEFINITIONS

In the context of a medical device, such as a dilator sheath assembly, "proximal" refers generally to the end of the assembly that is closest to the physician while "distal" refers generally to the end that is insertable into the patient. Where the terms "proximal-to-distal movement" or "proximal-to-distal force" are used, these terms can refer, without implying any limitation, to a situation where the device is being used with the patient, and also in an abstract context, where a physician and patient are not present, as well as to situations where testing is conducted in an engineering laboratory.

Blood that is "upstream" to a device may be "immediately upstream" to the device. Alternatively, blood that is "upstream" to a device is characterized in that the hemoglobin content, oxygen concentration, and carbon dioxide concentration, are essentially the same as blood that contacts the device. In another aspect, blood that is "upstream" to a device is characterized in that no major arteries or veins branch from the vessel in the region between the upstream blood and the device. Without limitation, blood that is "downstream" to a device may be "immediately downstream" to the device. In another non-limiting aspect, blood that is "downstream" to a device is characterized in that the hemoglobin content, oxygen concentration, and carbon dioxide concentration, of the blood are essentially the same as blood that contacts the device. In another aspect, blood that is "downstream" to a device is characterized in that no major arteries or veins branch from the vessel in the region between the downstream blood and the device. The present disclosure can, without limitation, be used for inserting into blood vessels or the heart, into the lymphatics, into cavities containing cerebrospinal fluid, into cavities containing renal filtrate (urological procedures), into the gastrointestinal tract, and the like.

DETAILED DESCRIPTIONS OF THE FIGURES

FIG. 1A identifies various angles. The depicted angles are generically disclosed, and are not all necessarily present in or relevant to any given embodiment. Unless indicated otherwise, angles are relative to the longitudinal axis (proximal to distal axis) of the dilator or to the longitudinal axis (proximal to distal axis) of the sheath. The small angles shown in the diagram reproduce the angles found in the device picture. Angle (1) refers to exterior (outside) distal taper of the dilator tip. Angle (2) refers to exterior (outside) proximal taper of the dilator tip. Where the term "chamfer"

is used, chamfer refers to angle (2) or equivalent. In embodiments, proximal taper shown at angle (2) can be substantially straight, or it can assume an S-curve. Angle (3) resides inside the dilator tip, that is, angle (3) resides inside the dilator's lumen. In embodiments, angle (3) can be zero degrees, that is, where the dilator is designed so that diameter (10 or 40) is equal to diameter (12 or 42), respectfully. Alternatively, angle (3) can be 0.1-0.2 degrees, 0.2-0.3 degrees, 0.3-0.4 degrees, 0.4-0.5 degrees, 0.5-0.6 degrees, 0.6-0.7 degrees, 0.7-0.8 degrees, 0.8-0.9 degrees, 0.9-1.0 degrees, 1.0-1.2 degrees, 1.2-1.4 degrees, 1.4-1.6 degrees, 1.6-1.8 degrees, 1.8-2.0 degrees, 2.0-2.2 degrees, 2.2-2.4 degrees, 2.4-2.6 degrees, 2.6-2.8 degrees, 2.8-3.0 degrees, or any combination of the above, for example, 1.8-2.6 degrees. Also encompassed are angles of about 1.0 degrees, about 2.0 degrees, about 5.0 degrees, about 10 degrees, about 15 degrees, about 20 degrees, about 25 degrees, about 30 degrees, and so on. Angle (4) is outside (exterior) proximal angle of sheath tip. Angle (5) is inside (lumen-side) of the sheath tip. The indicators numbered (1), (2), and (3), also serve to designate dilator tip. The indicators numbered (4) and (5) also serve to designate sheath tip. Unless specified otherwise, angles are those with the dilator and sheath in non-assembled state. In a preferred embodiment, angle (1) is 2 degrees.

In an exclusionary embodiment, the disclosure provides a dilator-sheath combination, where the dilator bump comprises a proximal taper angle (2), and where the proximal taper angle (2) of dilator bump is outside of the range of 40-50 degrees, with respect to the longitudinal axis, or where the angle is not 45 degrees, or where the angle (2) is greater than 90, 100, 120, 130, 140, 150, 160, or 170 degrees.

In some non-limiting embodiments, angles, width dimensions, and height dimensions, are essentially identical in the assembled state and in the non-assembled state.

Figure 1B:
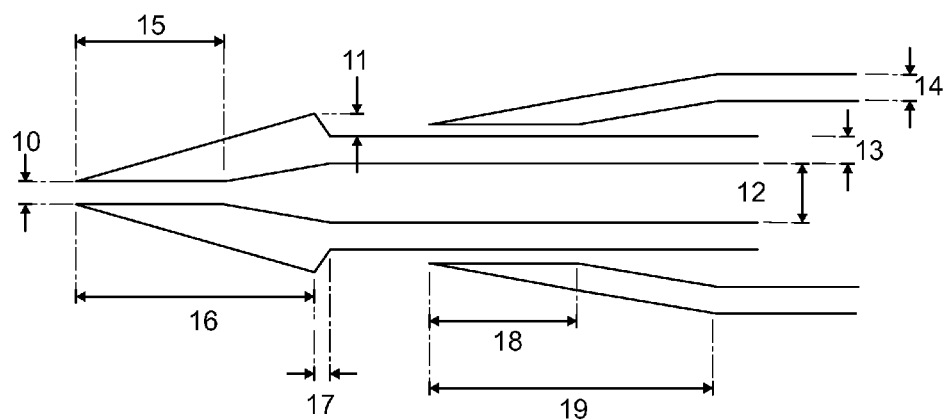

FIG. 1B identifies various widths and lengths. (Where a distance is relatively small, it is conventional in the draftsman's art to position the arrows on the outside, rather than on the inside, of the pair of indicator lines.) The depicted dimensions are generically disclosed, and are not all necessarily present in or relevant to any given embodiment. Distance (10) is inside diameter of the dilator tip, at the most distal part of the dilator tip. Distance (11) is height of dilator bump. Distance (12) is the inside (lumen-side) diameter of proximal region or main body region of dilator. Distance (13) is the width of the dilator body wall, situated proximal to of dilator tip. Distance (14) is the width of the sheath body wall, proximal to sheath tip. Distance (15) is the length of the interior (lumen-side) of dilator tip, where the interior of dilator tip has a region that has substantially parallel walls (parallel to the body of dilator). In embodiments, distance (15) can be essentially zero millimeters (mm), about 0.01 mm, about 0.02 mm, about 0.03 mm, about 0.04 mm, about 0.05 mm, about 0.1 mm, about 0.2 mm, about 0.3 mm, about 0.4 mm, about 0.5 mm, about 1.0 mm, about 2.0 mm, about 3.0 mm, about 4 mm, about 5.0 mm, any combination of these, and the like. Distance (16) is the length of the distal tapered region of dilator tip, where the distance is that indicated by a ruler that is parallel to the body of the dilator. (In other words, distance (16) is not that indicated by ruler that is in continuous physical contact with substantially the entire distal tapered region of the dilator tip.)

Distance (17) is the distance of proximal taper of dilator tip, where the distance is that indicated by a ruler that is parallel to the body of the dilator. Distance (18) is the length of distal end of sheath tip. In embodiments, distance (18) can be essentially zero millimeters, or it can be about 0.1 mm, about 1.0 mm, about 10 mm, and the like. Distance (19) is the length of tapered region of the sheath tip, as indicated by or as measurable by a ruler that is parallel to the body of the sheath. The ruler can be conceptual or it can be a real ruler.

Figure 1C:
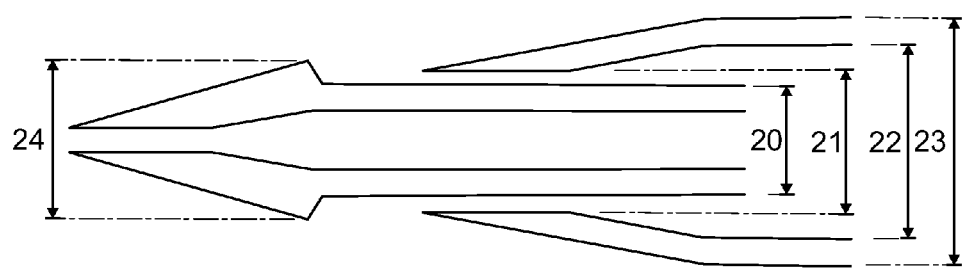

FIG. 1C discloses the outside diameter (20) of the body of the dilator, the inside diameter (21) (lumen-side) of the sheath tip, the inside diameter (22) of the region of the sheath that is immediately proximal to the sheath tip, and the outside diameter (23) of the region of the sheath that is proximal to the sheath tip and that is situated on the body of the sheath. Distance (24) is the maximal diameter of the dilator tip at dilator bump. Unless specified otherwise, the dimensions are those of the non-assembled dilator and sheath. The structure numbers are suitable for referring to dimensions when device is in both assembled state and in non-assembled state.

Figure 1D:
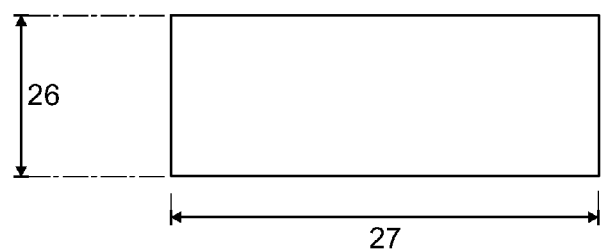

FIG. 1D discloses cylinder (25) with a length (27), and height (26), where this height is identical to that of the maximal diameter (24) of the dilator tip at the dilator bump. The cylinder may be used as a testing device for comparing: (1) The ability of the sheath tip to slide over the dilator bump, with: (2) The ability of the sheath tip to slide over the cylinder. Cylinder functions to provide a tube that is substantially longer than the proximal-to-distal distance of the region of the dilator tip bump that has a radius greater than the radius of the part of the dilator that is proximal to the dilator tip. The cylinder can have a length (27) that is about 0.1 mm, about 0.2 mm, about 0.5 mm, about 1.0 mm, about 2.0 mm, about 5.0 mm, about 10.0 mm, and the like. In embodiments, the cylinder is solid and non-deformable. Where the sheath tip is forced over the cylinder, the endpoint of the test is where crumbling or irreversible distortion of the sheath is encountered, or where friction effectively prevents further forcing of the sheath over the cylinder. The cylinder can be used to test, screen, and define, embodiments that are encompassed, and to test, screen, and define, embodiments that are to be excluded.

Figure 2A:
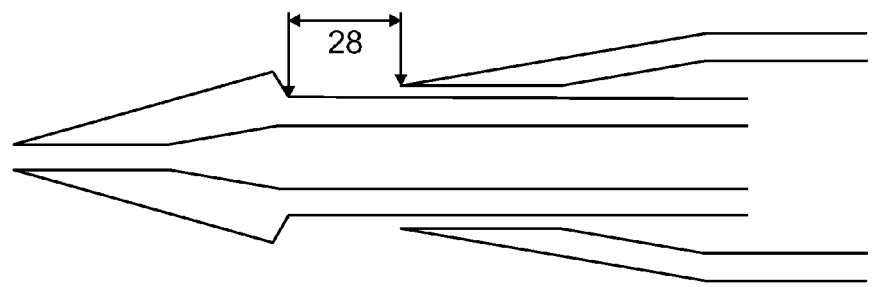
Figure 2B:
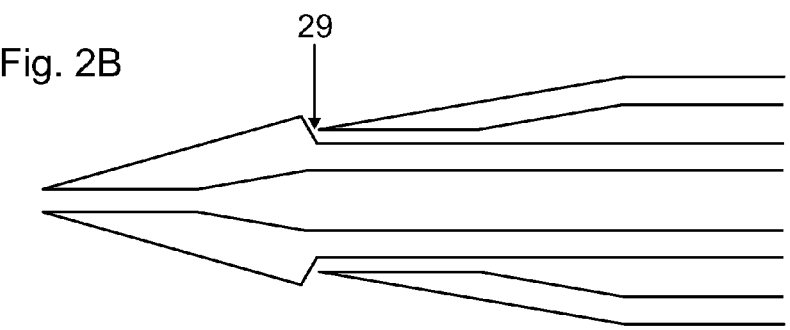

FIG. 2 discloses a non-limiting functional characteristic of embodiments of the dilator sheath assembly, according to the present disclosure. FIG. 2A shows a relaxed position (28), where (28) indicates a distance between the proximal terminus of the proximal taper of the bump, and the distal-most point of the sheath tip. FIG. 2B shows the sheath tip abutting the dilator bump, where the point of abutting is shown by (29). Sheath tip resides at distal end of sheath, and the terms "proximal portion of sheath tip" and "distal portion of sheath tip" can be used to refer to various parts of sheath tip.

The following concerns the point on the dilator tip and the point on the sheath tip. In a non-limiting preferred embodiment, the tip is not perfectly sharp, but is rounded and has a small but measurable diameter. The diameter of the rounded area can be, for example, 0.002 inches, 0.003 inches, 0.004 inches, 0.005 inches, 0.006 inches, 0.007 inches, 0.008 inches, 0.009 inches, 0.010 inches, 0.011 inches, 0.012 inches, and so on, and any combination, such as the range of 0.003 to 0.006 inches. The skilled artisan will understand that where a pie slice cut from a circle is not large enough to encompass a full diameter, a value for the rounded tip diameter can be extrapolated by way of an imaginary extension of the pie slice to a half circle or to a full circle. For the dilator tip, outer diameter of dilator tip is preferably 0.032 inches and inner diameter, 0.022 inches (thus, giving a rounded-tip diameter of 0.010 inches). For sheath tip, outer diameter of sheath tip is preferably 0.078 inches, and inner diameter of sheath tip is preferably, 0.073 inches (thus, giving rounded-tip diameter of 0.005 inches).

Figure 2C:
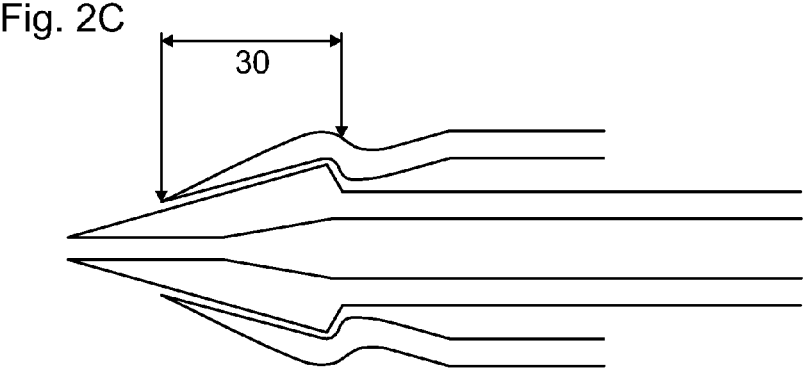

FIG. 2C shows the dilator sheath in a position where the sheath has been pushed over and stretched over the dilator bump, where the distance of pushing over is shown by (30). Testing has shown that it is not necessary for the sheath tip to abut the dilator bump, in order for optimal functioning of the dilator sheath during experimental insertions. In one aspect, when initiating insertion of the dilator sheath assembly, the distance (28) shown in FIG. 2A is about 0.0 mm, about 0.05 mm, about 0.1 mm, about 0.2 mm, about 0.4 mm, about 0.8 mm, about 1.0 mm, about 2.0 mm, about 3.0 mm, about 4.0 mm, about 5.0 mm, about 6.0 mm, about 8.0 mm, about 10.0 mm, and the like, or greater than 0.0 mm, greater than 0.05 mm, greater than 0.1 mm, greater than 0.2 mm, greater than 0.5 mm, greater than 1.0 mm, greater than 2.0 mm, and so on. In embodiments, where insertion results in the sheath stretched over the dilator bump, the sheath reverts to its original relaxed state. Where the plastic limit is overridden, the result can be breaking or splitting of the sheath, or it can be permanent expansion of the sheath. The function of preventing the plastic limit from being overridden can be a function of the following, group of four factors: (A) The material used; (B) The coefficient of friction; (C) The wall thickness; and (D) Elasticity.

FIG. 3 discloses angles and distances of rounded bump embodiments of dilator sheath assembly. FIG. 3A identifies angles. Angle (31) refers to the exterior (outside) distal taper of the dilator tip. Angle (32) refers to that of the distal face of the bump. In some embodiments, the distal face angle is equal to that of the proximal face angle, while in other embodiments the angles are different. Regarding angle (32), if the face has a portion that is substantially flat, that is, where it is possible to place a conceptual ruler or a real ruler on that flat portion, then angle (32) can be used. But where the distal face (or proximal face) is substantially rounded or curved or ovoid, and where application of a ruler only results in points that are tangential points, then the descriptor can be a radius (rather than angle).

In the case of an ovoid bump, an average radius may be used. Angle (33) refers to the inside (lumen-side) of the dilator tip. Angle (34) is the outside (exterior) proximal angle of the sheath tip. Angle (35) is the inside (lumen-side) of the sheath tip. Angle (36) refers to that between the proximal face of the dilator's bump and the longitudinal axis of the dilator. Regarding angles (32) and (36), these angles are measured from the imagined space within the dilator bump, and hence these angles will preferably be in the range of about 5 degrees to about 85 degrees. In one embodiment, both angles (32) and (36) are equal to each other, for example, about 5 degrees, 10, 15, 20, 25, 30, 35, 40, 45, 50, 55, 60, 65, 70, 75, 80, or about 85 degrees. In other embodiments, the respective angles can each approximately be, for example, 30 and 45, 30 and 60, 30 and 75, 45 and 30, 45 and 60, 45 and 75, 60 and 30, 60 and 45, 60 and 75, 75 and 30, 75 and 45, or 75 degrees and 60 degrees. Indicators (31), (32), (33), and (36), also serve to designate the rounded bump embodiment dilator tip. Indicators (34) and (35) designate the sheath tip. The disclosure encompasses embodiments where angle (35) is essentially zero degrees, that is, embodiments where diameter (21, 51) is essentially equal to diameter (22, 52). In an exclusionary embodiment, what can be excluded is embodiments where angle (35) is equal to zero degrees, when measured in assembled state, or when measured in non-assembled state. In other exclusionary embodiments, what can be excluded is embodiments where diameter (22, 52) is equal to diameter (23, 53), as measured in assembled state, or when measured in non-assembled state. The combination of indicators (31), (32), (33), and (36), refers to the bumped dilator tip. The combination of the indicators (34) and (35) refers to sheath tip, for use with bumped dilator.

Without implying any limitation, S-shaped bumps are also contemplated for dilator tip. In S-shaped embodiments, distal taper can be substantially straight and proximal taper S-shaped, distal taper can be rounded or ovoid and proximal taper S-shaped, distal taper can be S-shaped and proximal taper can be straight, distal taper can be S-shaped and proximal taper can be rounded or ovoid. Also, both the proximal and distal taper can be S-shaped.

A "rounded bump" is a bump situated at a dilator tip, where application of a ruler, plane, or straight edge, to at least 80% of the convex surface area (as viewed from a point that is perpendicular to the longitudinal axis of the dilator sheath assembly) results only in points of contact that are tangential. In this context, "application of a ruler" means incremental attempts to apply the ruler to the entire profile of the dilator tip. In another aspect, a "rounded bump" is a bump situated at a dilator tip, where application of a ruler, plane, or straight edge, to at least 90% of the convex surface area (as viewed from a point perpendicular to the longitudinal axis of the dilator sheath assembly) results only in points of contact that are tangential.

Figure 3A:
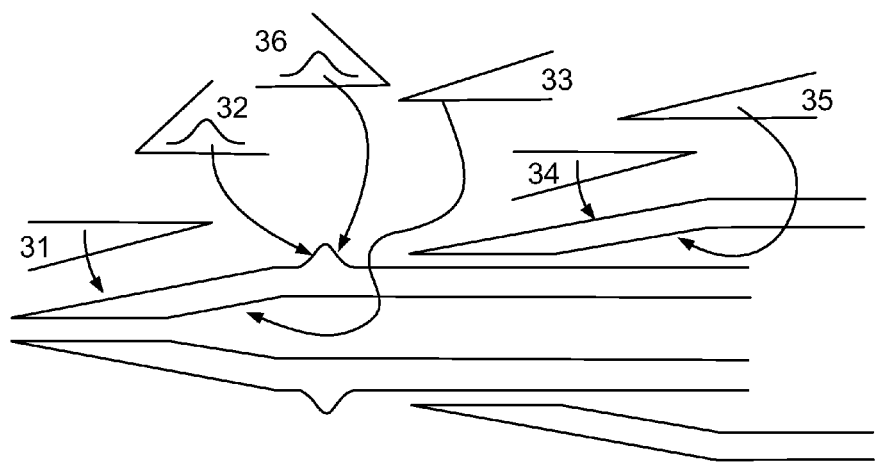
Figure 3B:
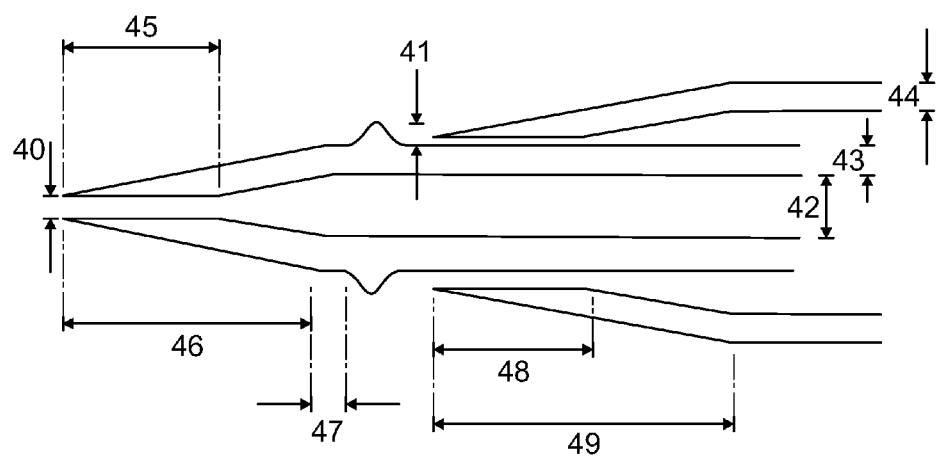

FIG. 3B identifies distances of a non-limiting rounded bump embodiment. Distance (40) is the inside (lumen-side) diameter of the dilator tip. Distance (41) is the height of the dilator bump. Distance (42) is the inside diameter of the proximal region or body of the dilator. Distance (43) is the width of the dilator wall, situated proximal to the dilator tip. Distance (44) is the width of the sheath wall, proximal to the sheath tip. Distance (45) is the length of the interior (lumen side) of the dilator tip, where the interior of the dilator tip has a region that has substantially parallel walls (parallel to the body of the dilator). In embodiments, distance (45) can be essentially zero millimeters, or it can be about 0.1 mm, 0.2 mm, 0.5 mm, 1.0 mm, 2.0 mm, 5.0 mm, or about 10 mm, and so on. Distance (46) is the length of the distal tapered region of the dilator tip, where the distance is that indicated by a ruler that is parallel to the body of the dilator. (In other words, this distance is not that indicated by a ruler that is in continuous physical contact with substantially the entire distal tapered region of the dilator tip.) Distance (47) is the length between the tapered part of the dilator tip and the bump. This distance (47) can be, for example, essentially zero millimeters, or about 0.01 mm, 0.02 mm, 0.05 mm, 0.10 mm, 0.12 mm, 0.15 mm, 0.20 mm, 0.50 mm, 1.0 mm, 1.5 mm, 2.0 mm, 2.5 mm, 5.0 mm, and the like. Distance (48) is the length of the interior portion (lumen-side) of the distal portion of the sheath tip. In embodiments, distance (48) can be essentially zero millimeters, or it can be about 0.1 mm, 0.2 mm, 0.5 mm, 1.0 mm, 2.0 mm, 5.0 mm, or about 10 mm, and the like. Distance (49) is the length of the tapered region of the sheath tip, as indicated by a ruler that is parallel to the body of the sheath.

Figure 3C:
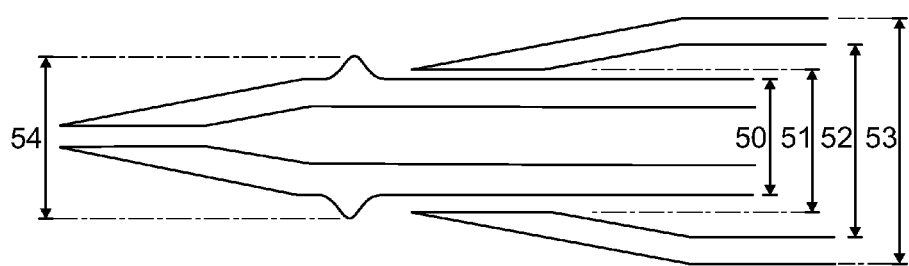

FIG. 3C reveals additional width generic, non-limiting dimensions of rounded bump embodiment of the dilator sheath assembly. Diameter (54) is the maximal width of dilator bump. Diameter (50) is the width of the outside diameter of the dilator, proximal to the dilator bump or in the body of the dilator. Diameter (51) is the inside diameter (lumen-side) of the sheath tip. In use, this diameter can be that of the sheath when the sheath is not assembled with dilator, or it can be that of the sheath with the sheath is assembled with dilator. Sheath tip is optionally configured so that, in the assembled dilator sheath, the sheath tip is elastically compressed against the body of the dilator. Hence, the diameter (51) can be lesser than the diameter (50) of the dilator body. Diameter (52) is the inner (lumen-side) of the sheath, in a region of the sheath that is proximal to the sheath tip, when contemplating non-assembled dilator sheath. Diameter (53) is the outer diameter of the sheath, in a region of the sheath that is proximal to the sheath tip. In certain non-limiting embodiments, the dimensions can be essentially the same when in the assembled state and non-assembled state.

Figure 3D:
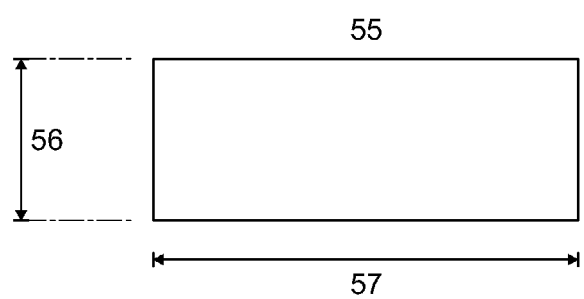

FIG. 3D discloses a cylinder (55) with a length (57), and width (56) where this width is identical to that of the maximal diameter (54) of the dilator tip at the dilator bump. The cylinder may be used as a testing device for comparing the ability of the sheath tip to slide over the dilator bump, with the ability of the sheath tip to slide over the cylinder. Use of this cylinder is further detailed elsewhere in this specification.

Figure 4A:
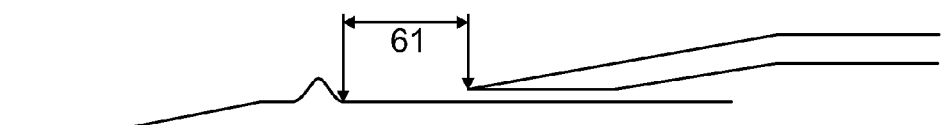
Figure 4B:
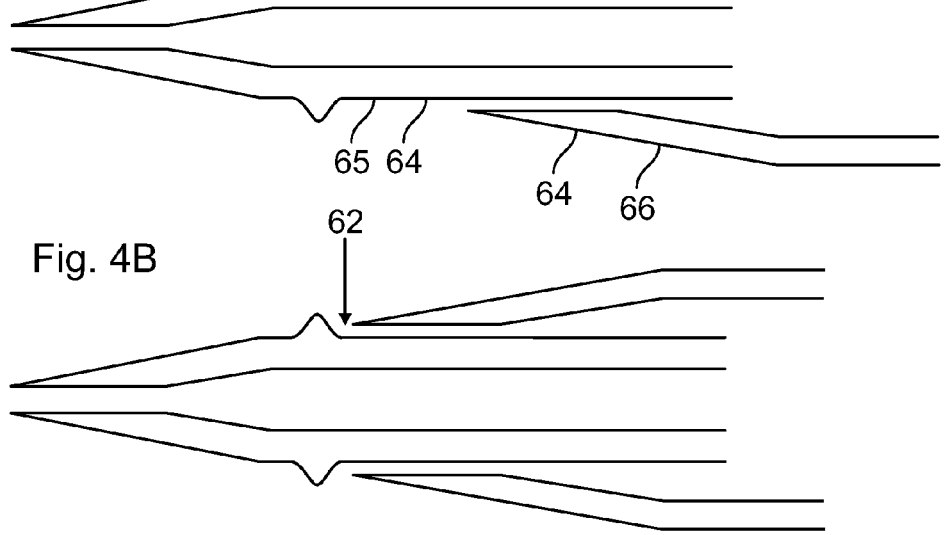
Figure 4C:
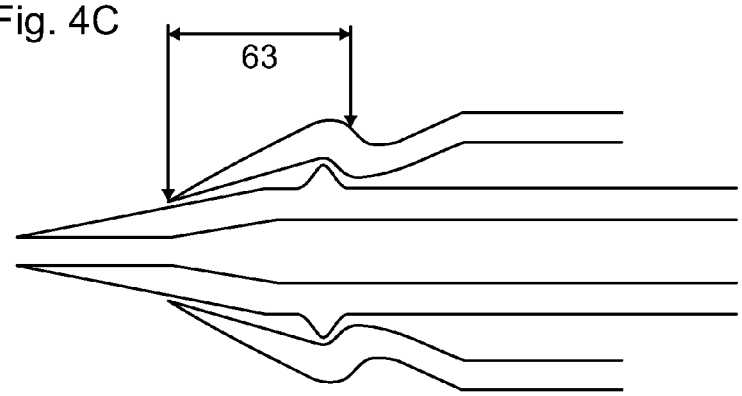

FIG. 4 reveals functional characteristics of embodiments of a non-limiting rounded bump embodiment of the dilator sheath assembly. FIG. 4A shows a relaxed position (61), where (61) indicates a distance between the proximal terminus of the bump, and the distal portion of the sheath tip. FIG. 4B shows the sheath tip abutting the dilator bump, where the point of abutting is shown by (62), and where this configuration is also relaxed. FIG. 4C shows the dilator sheath in a position where the sheath has been pushed over and stretched over the dilator bump, where the distance of pushing over is shown by (63). Testing has shown that it is not necessary for the sheath tip to abut the dilator bump, in order for the dilator sheath assembly to function optimally during insertion. In one aspect, when initiating insertion of the dilator sheath assembly, the distance (61) shown in FIG. 4A is greater than 0.0 mm, or the distance is about 0.05 mm, about 0.1 mm, about 0.2 mm, about 0.4 mm, about 0.8 mm, about 1.0 mm, about 2.0 mm, about 3.0 mm, about 4.0 mm, about 5.0 mm, about 6.0 mm, about 8.0 mm, about 10.0 mm, and the like. In embodiments, where insertion results in sheath stretched over dilator bump, as indicated in (63), completion of insertion is followed by the sheath reverting to its original relaxed state (61). Complete reversion, or 50% reversion, can occur, e.g., within 0.1 seconds, within 0.2 seconds, within 0.5 seconds, within 1.0 seconds, within 10 seconds, and so on. Insertion can result in stretching of the sheath over the dilator bump, where the device is configured so that the plastic limit is not overridden.

In other embodiments, structures, compositions, and lubricants (if any) are configured to minimize or prevent sheath from being stretched over dilator bump during insertion.

Dilator, sheath, or dilator sheath assembly is configured to prevent the plastic limit from being overridden, thereby resulting in permanent expansion of the sheath tip, permanent deformation of the sheath tip, or breakage of the sheath tip. In one aspect, the embodiment avoids the situation where a deformed sheath tip causes tissue damage when the sheath is withdrawn from the patient. Without implying any limitation, the function of preventing the plastic limit from being overridden can be a function of the following factors: (A) The material used; (B) The coefficient of friction; (C) The wall thickness; and (D) Elasticity.

In FIG. 4, number (64) refers to dilator sheath assembly, in a non-limiting generic aspect, including a dilator sheath assembly where the dilator has a dilator tip with a round bump, where the dilator tip has a non-round bump, and other embodiments. Structure (65) refers to dilator in a generic aspect, including dilator with a round bump at the dilator tip, dilator with a non-round bump at the dilator tip, and other embodiments. Structure (66) refers to sheath.

Minimizing Trauma and Tissue Damage when Removing the Dilator Sheath Assembly from the Subject's Body Spontaneous reversion from the position of FIG. 2C, thereby resulting in an assembly in the position of FIG. 2A, prevents or minimizes trauma and tissue damage to the patient when attempts are made to remove the dilator from patient's body. Also, this spontaneous reversion prevents or minimizes trauma and tissue damage when attempts are made to remove the sheath from patient's body, or when attempts are made to remove the dilator sheath assembly from patient's body. Deformation of the sheath tip effectively increases the diameter and abruptness of the structure that the physician is trying to pass through the tissue and vessel wall. The result is the inability to pass the device, consequently leading to the need to cut the skin with a scalpel to permit introduction or the need for an increase in the amount of force required to insert the feature potentially, thereby causing trauma to tissues or vessels. The dimensions, angles, configurations, and relative positions of the components of dilator sheath assembly, as set forth in these figures, and in all of the figures, are non-limiting.

Minimizing Trauma and Tissue Damage when Inserting the Dilator Sheath Assembly into the Subject's Body In embodiments, the diameter of the bump should be less than or equal to the outer diameter of the sheath body, when the dimensions are measured with the components (dilator; sheath) in their assembled state. Where the maximal diameter of the dilator bump is greater than the outer diameter of the sheath, when measured in assembled state, the result during insertion, and possibly also during withdrawal, could be bleeding around the insertion site. In a preferred non-limiting embodiment, diameter of dilator bump (24, 54) is about 0.012 inches larger than outer diameter (20, 50) of dilator body, as determinable for assembled dilator sheath.

In embodiments, maximal diameter (24, 54) of bump is about 20% less, about 15% less, about 10% less, about 9% less, about 8% less, about 7% less, about 6% less, about 5% less, about 4% less, about 3% less, about 2% less, about 1% less, essentially equal to, about 1% greater, about 2% greater, about 3% greater, about 4% greater, about 5% greater, about 10% greater, and the like, than the diameter (23, 53) of the sheath. Ranges that encompass two or more of the above parameters are also contemplated.

Assembled Versus Non-Assembled

In a preferred non-limiting embodiment, the maximum outer diameter of the dilator bump is the same, when comparing that with the non-assembled dilator sheath and with the assembled dilator sheath. Also, in a preferred embodiment, diameter of sheath body is not changed, when comparing that with the non-assembled dilator sheath with the assembled dilator sheath. Regarding interference, in a non-limiting preferred embodiment, fit between dilator and sheath leaves no gap at sheath tip, where absence of gap is ensured by an interference of 0.001 inch (meaning that when assembled, diameter of sheath tip increases by 0.001 inch). In embodiments, interference is less than 0.0005 inch, less than 0.001 inch, less than 0.002 inch, less than 0.004 inch, less than 0.005 inch, or less than 0.006 inch.

Each Embodiment can be Configured as a Series of French Sizes

The present disclosure provides a family of various embodiments, where the only difference between members of the family is that the French size of the body of the dilator is increased, and the French size of the body of the dilator is increased. Also provided is a family of various embodiments, where the French size of the body and tip of the dilator, as well as the French size of the body and tip of sheath, are increased. What is preserved in these embodiments is one or more of: (A) The function of minimizing or preventing trauma or tissue damage during insertion; (B) Minimizing or preventing trauma or tissue damage during removal of the dilator, sheath, or dilator sheath assembly from the patient, (C) Elastic recovery when the sheath has reverted to its original relaxed state; (D) Preventing splitting of the sheath during insertion of the assembly into the patient, or during removal from the patient; and (E) Maintaining the elastic limit.

Relative Diameters

In non-limiting embodiments, what is provided is a dilator sheath assembly, where the sheath distal tip diameter (21 in FIG. 1C; or (51) in FIG. 3C) is smaller than the inner diameter of the sheath body (22 or 52), where the distal tip diameter (21 or 51) of the sheath is smaller than the outer diameter (20 or 50) of the dilator body where said diameter is measured when the dilator is not assembled with the sheath, where the sheath comprises a distal taper and where the distal taper tapers from the outside diameter (23 or 53) of the sheath to the inside diameter (21 or 51) of the sheath, where the sheath body substantially comprises an elastomer, where the dilator is more rigid than the sheath body, where the outer diameter (24 or 54) of the dilator bump is greater than sheath tip diameter (21 or 51) and also where the outer diameter (24 or 54) of the dilator bump is greater than the sheath body inner diameter (23 or 52), where the outer diameter of the dilator bump (24 or 54) is greater than diameter (20 or 50) of the dilator's main body.

In one non-limiting embodiment, sheath tip diameter (51) is smaller than inner diameter (52) of the sheath body. In this embodiment, sheath tip diameter (51) is essentially equal to dilator body outer diameter (50). In non-limiting preferred embodiment, sheath tip inner diameter is 4-24 FR.

Comparing Ability of the Sheath to Pass Over Dilator Bump Versus Over a Cylinder with Same Diameter as Dilator Bump The following concerns sheath tip passing over dilator bump. In embodiments, sheath can pass over the dilator bump of outer diameter (24 or 54) but is not capable of passing over a cylinder (25 or 55) having a diameter (26 or 56) that is the same diameter as that of diameter (24 or 54), where the length of the cylinder that is employed for passing over is about 1.0 mm, about 2.0 mm, about 4.0 mm, about 6.0 mm, about 8.0 mm, about 10 mm, about 2 cm, about 4 cm, about 6 mm, and the like. In one aspect, attempts or tests at passing over the bump or passing over the test cylinder is entirely manual, without the aid of instruments such as tweezers, pumps, and the like. In the passing over test, the composition, surface layer or surface lubricant (if any), and radius, of the dilator that comprises the bump are identical to those of the comparator cylinder.

The following provides functional elements that can be used to define dilator sheath assembly. The definition is a functional definition. What is provided is dilator sheath where maximal diameter (24, 54) of dilator bump is, e.g., 2.5 mm, and where diameter (26) of cylinder is 2.5 mm, where the cylinder is 10 mm long, and where the dimensions, plastic polymers, and lubrication (if any), of the dilator sheath are configured so that transit of dilator over sheath, as set forth in FIG. 2A,B,C, occurs without damage to sheath and without irreversible deformation to sheath, but where transit of dilator over the test cylinder (25) does in fact result in damage to sheath or to irreversible deformation of sheath.

In other words, in non-limiting embodiments, dilator sheath can be configured to pass the first test, but to fail the second test (the second test is the cylinder test). In other words, the above provides a functional test to define a "sweet spot" in the structures and polymers some embodiments of the dilator sheath assembly.

The following concerns sheath body passing over dilator body. In non-limiting embodiments, diameter 22 (or 52) must be greater than diameter 20 (or 50), in order to provide clearance. In some aspects, 22 (or 52) is 0.01% greater than 20, 0.02% greater, 0.04% greater, 0.06% greater, 0.08% greater, 0.10% greater, 0.20% greater, 0.5% greater, 1.0% greater, 2.0% greater, 5.0% greater, 10% greater, 15% greater, 20% greater, and the like.

In embodiments, where sheath passes over bump without damage to sheath, with maintenance of elastic limit, sheath spontaneously reverts to distance 28 (or 61) (FIG. 2 or 4). This spontaneous reversion function can be maintained where the diameter of the bump increases and where the coefficient of friction decreases, or alternatively, where the diameter of the bump can decrease and the coefficient of friction increases. The coefficient of friction can be made to decrease, for example, by using a low-friction polymer or, alternatively, by using a lubricant. Coefficient of friction can be measured (see, e.g., Malkin and Harrison (1980) A small mobile apparatus for measuring the coefficient of friction of floors in J. Phys. D: Appl. Phys. 13 L77; Jay, et al (2007) Association between friction and wear in diarthrodial joints lacking lubricin in Arthritis Rheumatism. 56:3662-3669; Savescu, et al (2008) A technique to determine friction at the finger tips in J. Appl. Biomech. 24:43-50).

Polymers

Without imposing any limitation, preferred polymer for dilator comprises high density polyethylene, and preferred polymer for sheath can be one or more of polyurethane, ethylenetetrafluoroethylene (ETFE), or polyether block amide (Pebax). Pebax polymers are available, for example, from Arkema (King of Prussia, Pa.) and from Arkema, France. Without limitation, preferred is 69 Shore D HDPE for the dilator and 68 Shore D Pellethane for sheath.

French Size

The outside diameter of single lumen catheters, is often identified by gauge. The outside diameter of multi-lumen catheters are typically labeled by French size. The disclosure provides a tube (or medical conduit) with a French size that is, to provide non-limiting examples, 3 Fr (1 mm; 0.039 inches), 4 Fr (1.35 mm; 0.053 inches), 5 Fr (1.67 mm; 0.066 inches), 6 Fr (2 mm; 0.079 inches), 7 Fr (2.3 mm; 0.092 inches), and so on. The corresponding diameters in millimeters and inches are shown in parenthesis. The French system has uniform increments between gauge sizes (⅓ of a millimeter) (Iserson K V (1987) J.-F.-B. Charrière: the man behind the "French" gauge. J. Emerg. Med. 5:545-548). Systems for measuring the outside diameter and inside diameter (lumen) of catheters, needles, and the like have been described (see, e.g., Ahn, et al. (2002) Anesth. Analg. 95:1125). French size can refer to an inside diameter or to an outside diameter (see, e.g., U.S. Pat. No. 7,641,645 issued to Schur, which is hereby incorporated by reference).

Sheaths, Dilators, Hubs, Cannulae, and Catheters

A sheath is generally constructed with a hub at its proximal end. The hub can serve as a mating point for a dilator, as a handle for applying torque, as a grip for holding the instrument, as a grip for applying longitudinal force, as a branching point of tabs or wings for use in splitting a splittable sheath, and as one of the components that is split (when part of a splittable sheath) in order to clear the catheter (see, e.g., U.S. Pat. No. 6,796,991 issued to Nardeo, US2010/0292647 of Nardeo, et al, US2009/0143739 of Nardeo, which are incorporated by reference). Where a sheath has a relatively large diameter or has a blunt distal point, dilator can be used to aid in the insertion of the sheath into the patient. Dilator has a long tubular section, the outside diameter of which is slightly smaller than the inside diameter of the sheath. Dilator has a hollow center which runs along the entire length of the dilator, and the dilator also has a pointed tip on its distal portion. A hub can reside on the proximal end of the dilator, where this hub can provide a handle to aid in guiding the dilator into a vessel, and for coupling of the dilator hub to the sheath hub.

Dilator Tip Embodiments

Dilator tip of the present disclosure can, without implying any limitation, have a conformation where the tip includes a proximal taper and a distal taper, where the proximal taper (or distal taper) occurs at a slight angle with reference to the longitudinal axis of the dilator, for example, at an angle greater than 0 degrees, greater than 1°, 2°, 4°, 5°, 10°, 15°, 20°, 25°, 30°, 35°, 40°, 45°, 50°, 55°, 60°, 65°, 70°, 75°, 80°, and greater than 85°, and the like. Without implying any limitation, what is encompassed is any combination of the above angles for the proximal taper angle and distal taper angle, as it applies to a dilator tip, or to a sheath tip. In embodiments, sheath tip has only a distal taper (and not any proximal taper).

Diameter of the highest region of the bump is compared with the diameter of the distal sheath tip, where the diameter of the distal sheath is measured across the length of the sheath's lumen, from inner face to inner face. In a first aspect, the bump diameter and sheath diameter are measured where the dilator and sheath are not assembled, for example, where the dilator and sheath are laying side-by-side. In a second aspect, the bump diameter and sheath diameter are measured where the dilator and sheath are assembled, and where the distal tip of the sheath is at a distance that is near the proximal-most point of the bump, but where the sheath tip does not quite abut the bump.

In the first aspect, as well as in the second aspect, the diameter of the highest region of the bump is greater than the diameter of the sheath tip (measured as above), where the bump has a diameter that is at least 5%, at least 10%, at least 15%, at least, 20%, at least 25%, at least 30%, at least 35%, at least 40%, at least 45%, at least 50%, at least 55%, at least 60%, at least 65%, at least 70%, at least 75%, at least 80%, at least 90%, at least 100%, at least 120%, at least 140%, at least 160%, at least 180%, at least 200%, and the like, greater than the sheath tip diameter.

Diameter of tubular body of dilator, that is, the part of the dilator that begins just proximal to the dilator bump (and that extends for some distance in the proximal direction) is compared with the diameter of distal sheath tip, where diameter of distal sheath tip is measured across the length of the sheath's lumen, from inner face to inner face. In a first aspect, the dilator body diameter and sheath tip diameter are measured where the dilator and sheath are not assembled, for example, where the dilator and sheath are laying side-by-side. In a second aspect, the dilator body diameter and sheath tip diameter are measured where the dilator and sheath are assembled, and where the distal tip of the sheath is at a distance that is near the proximal-most point of the bump, but where the sheath tip does not quite abut the bump.

In the first aspect, as well as in the second aspect, the diameter of the dilator body is greater than the diameter of the sheath tip (measured as above in assembled or, alternatively when non-assembled), where the dilator body has a diameter that is at least 5%, at least 10%, at least 15%, at least, 20%, at least 25%, at least 30%, at least 35%, at least 40%, at least 45%, at least 50%, at least 55%, at least 60%, at least 65%, at least 70%, at least 75%, at least 80%, at least 90%, at least 100%, at least 120%, at least 140%, at least 160%, at least 180%, at least 200%, and the like, greater than the sheath tip diameter.

Methods Embodiments

The disclosure encompasses methods of use and methods of manufacturing. What is provided is a method encompassing a step of assembling the non-assembled dilator and sheath, inserting assembly over a guide wire, step of subcutaneous insertion, step of insertion of the assembly into a vessel or cavity, such as a blood vessel, lymphatic vessel, ureter or bladder, or cavity in the vertebral column or skull. What is also provided is the step of using the assembly to facilitate the insertion of a cannula, catheter, needle, stent, balloon, or component of a medical device. Moreover, what is provided is the step of introducing a drug, radiopaque substance, or pharmaceutical, or the step of removing a bodily fluid, a blood sample, a biopsy, and the like. In manufacturing methods embodiments, what is provided is the step of molding, polymerizing, trimming, shaving, cleaning, polishing, applying a colorant or dye, fitting, assembling, packaging, with regards to the sheath, dilator, valve, coupler, lock, ring, seal, annulus, or any combination of the above. Also provided is the step of applying or removing an adhesive or a lubricant to one or more of said components.

Components for the methods and devices of the disclosure are available, for example, from any major medical device company, for example, Medtronic of Minneapolis, Minn.; Advanced Cardiovascular Systems in Santa Clara, Calif.; Baxter International of Deerfield, Ill.; Abbott Laboratories at Abbott Park, Ill., Edwards Lifesciences, Irvine, Calif., and Boston Scientific of Natick, Mass. Components of the present disclosure can be made, without limitation, by molding, blow molding, slush molding, injection molding, rotational molding, compression molding, extrusion, thermoforming, stamping, calendaring, and so on (Brazel, C S; Rosen, S L (2012) Fundamental Principles of Polymeric Materials. Wiley, Hoboken, N.J.).

In one embodiment, the dilator bump is not inflatable. In another non-limiting embodiment, the dilator bump is inflatable.

The hardness of the devices of the present disclosure, including hardness of specific features, such as a tip, wall, bump, or tapered region, can be measured by the durometer method and Shore hardness scale. Hardness tests, as well as relative hardnesses of polyethylene, polyurethane, and polypropylene, are disclosed (see, e.g., Ashby M F, Jones D R H (2012) Engineering Materials 1, $4^{th}$ ed., Elsevier, New York, pp. 115-133). In non-limiting embodiments, the dilator is harder than the sheath, for example, the dilator tip is harder than the sheath tip, where the hardness is at least 1.0 Shore A units harder, at least 2 Shore A units harder, at least 5 units, at least 8 units, at least 10 units, at least 12 units, at least 14 units, at least 16 units, at least 18 units, at least 20 units, at least 25 units, at least 30 units, at least 35 units, at least 40 units, at least 50 units, at least 60 units, and the like, harder on the Shore A units scale. The Shore D, combinations of Shore A and Shore D, or other Shore units, may also be used to characterize embodiments of the present disclosure.

EXAMPLES

Example 1

The following example involved thin film testing. Comparative testing of three different sheath tips was conducted, where the tests were conducted with a thin polymer film (FIGS. 5 and 6). The thin polymer film was 0.015 inch thick natural polyurethane from Stevens Urethane P/N ST-1880 (Easthampton, Mass.). Insertion force was measured with an MTS Universal Testing Machine with a 50 Newton (N) load cell. The test stand advances the sheath-dilator assembly through the film at a controlled rate. The film was perforated with a needle prior to insertion. The needle was a 21 GA introducer needle. Testing was with an assembled dilator-sheath. The three tips that were tested were as follows:

(1) A preferred embodiment sheath tip (45 degree chamfer) (gmf) (squares),
(2) Predicate sheath tip (gmf) (diamonds), and
(3) Competitor sheath tip (gmf) (solid dots) (FIG. 5).

The insertion force is shown in units of gmf. The sheaths were identical for the preferred embodiment (45 degree chamfer) and Predicate, but the competitor testing used the competitor sheath and competitor dilator.

The graph shows percent insertion is greater, for any given insertion force (gmf) for the preferred embodiment (squares), lesser for the predicate sheath tip (diamonds), and somewhat lesser for the competitor sheath tip (solid dots). The mean gmf for the preferred embodiment (363.5 gmf) (SD=30.04), predicate (409.4 gmf) (SD=33.51), and competitor (418.9 gmf) (SD=43.90) are indicated. The materials used for the preferred embodiment (45 degree chamfer) are as follows. The sheath body resin is Pellethane® (Base Resin Dow Chemical 2363) with 20% barium sulfate and 1% titanium dioxide. The Pellethane® is a blend of two different hardnesses—59% 75 shore D and 20% 80 shore A. The dilator body resin is Paxon® (HDPE) 69 shore D (Base Resin Exxon Mobil AL55-003) with 20% barium sulfate. APPENDIX ONE discloses methods that were used for the polymer film testing.

In insertion force embodiments, present disclosure comprises dilator sheath combination where at least 50% insertion occurs with an insertion force of 380 gmf, with an insertion force of 370 gmf, with an insertion force of 360 gmf, or with an insertion force of 350 gmf, and the like. In exclusionary embodiments, what can be excluded is dilator sheath assembly, where less than 50% insertion occurs with an insertion force of 350 gmf, 360 gmf, 370 gmf, 380 gmf, 390 gmf, 400 gmf, 410 gmf, 420 gmf, 430 gmf, 440 gmf, 460 gmf, or 470 gmf, and so on. In other exclusionary embodiments, what is excluded is a dilator-sheath combination that also has a needle, for example, a needle that is inserted through the dilator, or a needle that is inserted through the sheath, or a needle included in a package that holds dilator and sheath.

Embodiments where Dilator is Relatively Incompressible, with Respect to Sheath

The present disclosure encompasses a dilator that is incompressible, relative to the sheath, where this relative incompressibility results is a function of structural dimensions and compositions of the dilator and structural dimensions and compositions of the sheath, and of any lubricant used.

FIG. 6 provides a boxplot of 6 French sheath tip penetration force. The data in this figure demonstrate that the preferred embodiment (45 degree chamfer) has the lowest sheath tip penetration force, with the penetration forces for the predicate higher, and competitor the highest. The upper whisker extends to maximum data point within 1.5 box heights from top of box. For each data set, the upper area represents third quartile (75% of data less than or equal to the top line), where the bisecting line is the median (50% of data less than or equal to line), and the lower area is first quartile (25% of data less than line). The lower whisker extends to a minimum data point within 1.5 box heights from bottom of box. The asterisks represent a statistical outlier beyond upper or lower whisker. Boxplots allow one to quickly evaluate the distribution of data for shape, central tendency, and variability.

Table 2 discloses dimensions, resin or polymer, and lubricant, used for a non-limiting preferred embodiment (45 degree chamfer), the predicate embodiment, and the competitor embodiment, used to generate the data in FIGS. 5 and 6.

TABLE 2

Dimensions and compositions of dilator and sheath used for comparative testing

| Dimension ID | Description | Units | Preferred embodiment | Predicate embodiment without radially enlarged dilation feature (characterized in FIGS. 5&6) | Embodiment with radially enlarged dilation feature and chamfer (characterized in FIGS. 5&6)) | Competitor (characterized in FIGS. 5&6)) |
|---|---|---|---|---|---|---|
| A | Dilator tip inner diameter | inches | .022 | .022 | .022 | .025 |
| B | Dilator tip taper angle angle | degrees | 3-5 | 4 | 4 | 4 |
| C | Dilator Rear Taper Radius #1 | inches | .030-.120 | N/A | 45 degree chamfer | N/A |
| D | Bump offset | inches | .0045-0075 | 0.000 | .007 | 0 |
| E | Sheath tip wall thickness at point of tangency | inches | .003 | .003 | .003 | .004 |
| F | Sheath tip taper angle | degrees | 4-6 | 5 | 5 | 3.5 |
| G | Gap between sheath body | inches | .001-.003 | .003 | .003 | .002 |

TABLE 2-continued

Dimensions and compositions of dilator and sheath used for comparative testing

| Dimension ID | Description | Units | Preferred embodiment | Predicate embodiment without radially enlarged dilation feature (characterized in FIGS. 5&6) | Embodiment with radially enlarged dilation feature and chamfer (characterized in FIGS. 5&6)) | Competitor (characterized in FIGS. 5&6)) |
|---|---|---|---|---|---|---|
| | inner diameter and dilator body outer diameter | | | | | |
| H | Sheath body wall thickness | inches | .005-.010 | .010 | .010 | .006 |
| I | Sheath tip inner diameter | inches | .040-.75 | .084 | .084 | .083 |
| J | Interference between sheath tip and dilator body | inches | .0005 | .0005 | .0005 | 0 |
| K | Dilator body outer diameter | inches | .040-.75 | .085 | .085 | .083 |
| L | Dilator rear taper radius #2 | inches | .030-.120 | N/A | N/A | N/A |
| Longitudinal stretch | — | Percent (%) | 0-3% of sheath body length | 0-3% of sheath body length | 0-3% of sheath body length | — |
| Sheath material | — | N/A | Pellethane blend (polyurethane) | Pellethane blend (polyurethane) | Pellethane blend (polyurethane) | ETFE |
| Dilator material | — | N/A | High density polyethylene | High density polyethylene | High density polyethylene | Polypropylene |
| Coefficient of friction | — | Dimensionless | 0.00-0.50 | 0.00-0.50 | 0.00-0.50 | — |
| Lubricant | — | N/A | Petrolatum or Silicone Oil | Petrolatum | Petrolatum | — |

In embodiments, what is provided is a dilator sheath assembly, or dilator sheath combination, where the material used, the coefficient of friction, the wall thickness, and the elasticity, are configured to require an insertion force of less than 350 gmf to succeed in at least 20% insertion, according to the test disclosed in FIG. 5, to succeed in at least 25% insertion, at least 30%, at least 35%, at least 40%, at least 45%, at least 50%, at least 55%, at least 60%, at least 65%, at least 70%, or at least 75% insertion, according to the test disclosed in FIG. 5. In other embodiments, what is provided is a dilator sheath assembly, where the material used, the coefficient of friction, the wall thickness, and the elasticity, are configured to cooperate with each other to require at least 10 gmf lesser insertion force to achieve 50% insertion (compared to competitor's device of FIG. 5), to require at least 15% lesser insertion force (gmf); to require at least 20%, 25%, 30%, 35%, 40%, 45%, 50%, 55%, 60% lesser insertion force to achieve 50% insertion, and so on, than when using the competitor's device of FIG. 5.

Example 2

The following example used porcine skin testing. The potential for sheath tip deformation upon insertion through porcine tissue was measured. What was compared was insertion of the standard sheath and dilator and the standard sheath with a non-limiting preferred embodiment (45 degree chamfer) dilator and the predicate dilator. The non-limiting preferred embodiment (45 degree chamfer) dilator allowed for 29/31 sheaths to be inserted through the porcine tissue without any damage. But with the standard dilator, the standard dilator only allowed 6/32 sheaths to be inserted without any damage. This represents a 75% improvement in performance, or a 59%-91% improvement with 95% confidence.

Test Medium

Porcine skin collected from pig feet was used for testing. Animals aged about 2 years yield usable skin. The skin was from Animal Technologies, Inc. (Tyler, Tex. 75702). Skin is delivered either fresh, on ice, or frozen. Porcine skin from other areas on the body as well as other animal skin, for example, bovine, ovine, canine, and the like, may be used for testing. Because of the variation in thickness and resistance to penetration across the tissue sample, it is necessary to identify an area that both allows sheath and dilator assemblies to be inserted through the sample, but that also causes the control sample to fail during approximately 50% or greater of insertions.

Using control assemblies, test multiple areas on the skin in order to block out a region that will suffice for the test. Once identified, maximize the use of this region by inserting each assembly per the procedure below approximately ⅛ inch away from the previous insertion.

In Vitro Insertion Testing of Sheath and Dilator Assemblies Through Animal Tissue Set up a designated testing area with absorbent towels or drapes. Acquire and put on gloves as a means of Personal Protective Equipment (PPE). Acquire the number of dilators and sheaths needed for testing. 6 FR sheath and a variety of dilator samples are required as control samples. All insertion components are necessary, including a spring wire guide (SWG) and needle or catheter-over-needle. Remove thawed or fresh porcine skin from the packaging. The procedure is as follows:

Insert the entire length of dilator through hemostasis valve into sheath, pressing hub of dilator firmly into hub of hemostasis valve/side port assembly until snap-lock is engaged.

1. For sheaths coated with a hydrophilic solution, submerge the assembly in water or saline for at least 10 seconds prior to insertion.

2. Using the introducer needle or needle over catheter, puncture the skin at a 15-30° angle, penetrate completely through the skin, needle bevel up. The operator will need to use the hand not holding the needle to grasp and stabilize the porcine skin sample.

3. Insert soft tip of spring wire guide (SWG) through introducer.

4. Hold SWG in place and remove the introducer. Replace needle guard or use other suitable sharps device to prevent accidental needle stick.

5. Thread tapered tip of dilator/sheath assembly over SWG. Grasping near skin, advance assembly through the skin with slight twisting until the sheath pokes through the opposite side of the skin sample.

Once the dilator/sheath assembly is through the skin inspect the sheath tip for accordion like tip deformation as, as well as any other type of tip deformation. Record results on attached sheet using noted criteria. Alternating between test specimens and control samples, repeat steps in the procedure, with the required number of samples. Each new insertion should be approximately ⅛ inch away from the previous insertion and samples need to be alternated to prevent tissue variability from being a factor in the rate of failure.

If disposing of the skin after testing it must be disposed of in a biohazard bag; otherwise, repackage the skin and replace in a biohazard refrigerator for storage, and clean up the work area with isopropyl alcohol or other suitable disinfectant. The result criteria are as follows: (A) Sample passed through skin with no damage; (B) Sample passed through skin with damage; (C) Sample could not be passed through skin because of sheath deformation; (D) Sample could not be passed through skin because of high insertion force, but no sheath damage observed.

Spring-Wire Guide

The following is non-limiting background information on spring-wire guide. The Seldinger method can be used to insert a venous catheter. This technique involves locating the vein using an introducer needle, or a catheter over a needle, then introducing a spring-wire guide through the needle or catheter, and then threading a venous catheter over the wire to the proper depth. Using a spring-wire guide allows for use of a small needle to ultimately place a much larger catheter. Spring-wire guides are strong but flexible enough to conform to angles of blood vessels. The tips are soft to prevent damage to vessel walls (Arrow Multi-Lumen Central Venous Catheter Nursing Care Guidelines (1996) Arrow Int., Inc. 40 pages).

Example 3

A 3-dimensional diagram of a generic embodiment is disclosed in FIG. 7. Starting from the distal end, (71) is the sheath tip, (72) is the sheath body, (73) is the sheath housing (also called sheath hub), (74) indicates the general position of the sheath aperture (not visible in this view, but visible when viewed from the proximal end), (75) is the dilator tip, (76) is the dilator bump (also called radially enlarged dilation member), (77) is the dilator shaft (also called elongate dilator shaft), and (78) is the dilator hub or coupler. The fin in the dilator hub and the groove in the sheath hub is a non-limiting coupling mechanism.

Example 4

FIG. 8 discloses structures and characteristics of embodiments that prevent deformation of the sheath distal tip, for example, in clinical use in a patient, in experimental testing, or in quality control testing. The diameter of the sheath distal tip (87; 97), when assembled in the dilator-sheath assembly, is less than the maximal diameter (86; 96) of the dilator bump (82; 92) as shown. In other words, the thinnest region of the sheath tip resides in the "shadow" (84; 94) of the dilator bump, and does not encounter resistance when inserted into or pulled out of tissues in a patient. The shadow region is indicated by the dashed lines (84) in FIG. 8A and (94) in FIG. 8B. Resistance to tissue can occur at regions of the sheath, indicated by 88 (FIG. 8A) and 98 (FIG. 8B), that are proximal to the "shadow" region. By preventing deformation of the sheath distal tip, the device and methods of the present disclosure prevent trauma and injury to the patient's tissues, inflicted by the deformed sheath tip, during insertion or withdrawal of the sheath.

FIG. 8 identifies distal taper of dilator tip (81; 91), dilator tip bump (82; 92), proximal taper of dilator tip (83; 93), shadow region (84; 94), sheath tip (85; 95), maximal diameter of dilator bump (86; 96), diameter of sheath distal tip (87; 97); region of sheath (88; 98) that is distal to sheath tip that encounters resistance to tissues when in use. In FIG. 8B, the space (99) between the inner (lumenal) surface of the body of the sheath and the outer surface of the body of the dilator, serves the following function. The function is to facilitate, and in some embodiments is required for, passage of the dilator bump through the entire sheath lumen during assembly or disassembly. The space (99) is indicated by the inverted arrows, as is conventional in mechanical drawings. Distance (100) is the length of the sheath distal tip, in sheath embodiments that include space (99). In embodiments, the ability of the dilator bump to pass through sheath body can be a function of one or more of the following: (A) Space (99); (B) Elasticity of sheath; (C) Lubrication; and (D) Relative short length of distance (100). The present disclosure includes, any combination of these structural features (i.e., distances), compositional features (i.e., lubrication), and functional features (i.e., elasticity). In embodiments, the combination of the space (99), elasticity of sheath, lubrication, and short distance of (100), allows the dilator bump to pass through the sheath body with little or no plastic deformation of the sheath. The function of preventing plastic deformation of the sheath ensures that the diameter of the sheath tip remains less than the diameter of the dilator bump (except when the dilator bump is actually passing through the sheath tip).

Shadow Region and Radial Diameter of Shadow Region

FIG. 8A shows shadow region, where interior diameter of sheath tip is same as interior diameter of body of sheath. FIG. 8B shows shadow region, where interior diameter of sheath tip contacts dilator, but interior diameter of sheath body, at least in non-assembled state, does not contact sheath body, or less firmly contacts sheath body. FIG. 8C is a legend, which applies to both FIG. 8A,B, showing radial distance of sheath shadow, and 50% of radial distance of sheath shadow. The present disclosure encompasses, and is not limited to, dilators and sheaths that, in their assembled state, produce a shadow where radial distance of the shadow is at the 100% size (structure 200) (see legend, FIG. 8C). Also encompassed, is dilators and sheaths that, in their assembled state, produce a shadow where the radial distance of the shadow is at the 50% size (structure 201) (see legend, FIG. 8C).

Abutting Embodiments

Figure 9B:
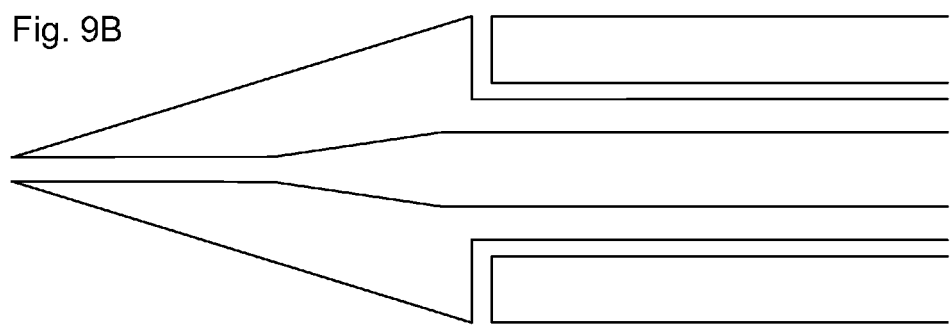
Figure 9C:
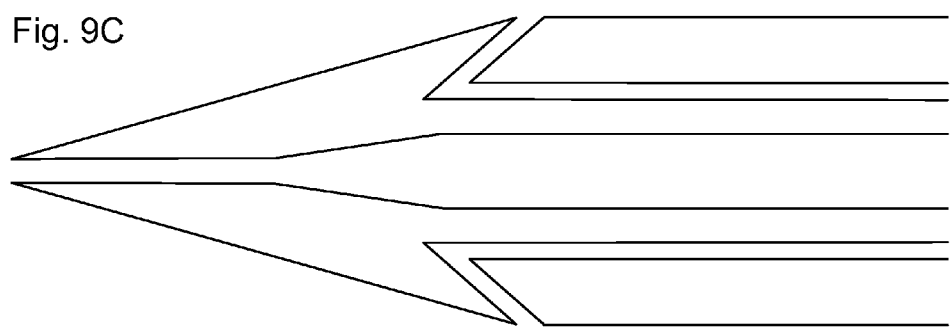

In some embodiments, the disclosure encompasses one or more face-to-face embodiments (FIG. 9). What can be encompassed is a face-to-face embodiment that is formed when dilator and sheath are coupled together or are locked together. Alternatively, what can be encompassed is a face-to-face embodiment that is formed when dilator and sheath are coupled, but where sheath and dilator are forced to move towards each other, and sheath elastically stretches and sheath tip moves towards dilator bump. In exclusionary embodiments, the disclosure does not encompass one or more face-to-face embodiments. In other exclusionary embodiments, what can be excluded is a face-to-face embodiment that is only formed in the condition when dilator and sheath are coupled and where sheath and dilator are forced to move towards each other, e.g., as when pushing the assembled device into a patient or when retracting the assembled device from the patient. "Face-to-face" refers a configuration where, for example, distal terminus of sheath and proximal terminus of proximal taper of dilator can contact each other, where the contact occurs in a substantially planar region of mutual contact. In the face-to-face configuration, the substantially planar region of mutual contact can be perpendicular to longitudinal axis of dilator-sheath assembly (FIG. 9B). Alternatively, in the face-to-face configuration, the substantially planar region of mutual contact can be tilted distally (FIG. 9A), or the substantially planar region can be tilted proximally (FIG. 9C). In embodiments, what can be excluded is a device, a combination, or an assembly, that has any face-to-face configuration, that has FIG. 9A configuration, that has FIG. 9B configuration, or that has FIG. 9C configuration. The present disclosure encompasses rounded-corner embodiments of FIG. 9, e.g., where about 5%, about 10%, about 15%, or about 20%, of what is otherwise a flat surface takes the form of a rounded-corner. What can be excluded is the FIG. 9 embodiments that take a rounded-corner configuration.

In other exclusionary embodiments, what is excluded is dilator-sheath assembly, or dilator-sheath combination, where region of dilator that is just proximal to dilator bump has a recessed annulus, or a recessed band, or a tapered recessed band. What can also be excluded is a recessed annulus configured for accepting sheath tip, that is, configured for stabilizing position of sheath tip. In other exclusionary embodiments, what is excluded is a dilator-sheath assembly, or dilator-sheath combination, that includes a rod for pushing a medical device into position, such as a medical device that is a stent or balloon.

Moreover, the disclosure encompasses embodiments where the radial distance of the shadow is about 5%, about 10%, about 20%, about 30%, about 40%, about 50%, about 60%, about 70%, about 80%, about 90%, about 100%, about 120%, about 140%, about 160%, and the like. Also encompassed are embodiments were the radial distance of the shadow is less than 100%, less than 110%, less than 120%, less than 130%, less than 140%, less than 150%, and so on. Moreover, what is encompassed are embodiments where radial distance is at least 5%, at least 10%, at least 20%, at least 40%, at least 50%, at least 60%, at least 70%, at least 80%, at least 90%, at least 100%, but less than 105%.

The radially enlarged dilation member is capable of being passed through the sheath body and tip due to elasticity of the sheath material, additional clearance between the sheath body and maximum dilator diameter, and low coefficient of friction between the dilator and sheath. A variety of sheath materials may be chosen provided they have sufficient elasticity to expand over the maximum diameter of the dilation member and return to a relaxed state with minimal plastic deformation such that the radial extension of the sheath tip end wall remains less than the radial extension of the dilation member. The elastic contact between the nominal inner diameter of the sheath tip and the diameter of the shaft of the dilation member is 0.001 inch (0.001 inch interference) and the sheath tip is capable of at least 17% strain with less than 2% plastic deformation. The diameter of a representative 6 French sheath tip is 0.084 inches at rest, expands to 0.099 inches as the dilation member is passed through the sheath, and returns to approximately 0.085 inches. The ability to pass the dilation member through the sheath is improved by the addition of a medical grade lubricant to the inner surface of the sheath body.

In embodiments where the dilator-sheath assembly, or dilator sheath combination, has interference, interference can be 0.0005-0.001 inch, 0.001-0.002 inch, 0.002-0.003 inch, 0.003-0.004 inch, 0.004-0.005 inch, 0.005-0.006 inch, 0.006-0.007 inch, 0.007-0.008 inch, 0.008-0.009 inch, 0.009-0.010 inch, or in a greater range. Also contemplated is any combination of the above ranges, for example, interference of 0.001-0.005 inch, or 0.002-0.008 inch. Moreover, embodiments include interference that is at least 0.0005 inch, 0.001 inch, at least 0.002 inch, at least 0.003 inch, at least 0.004 inch, at least 0.005 inch, at least 0.006 inch, at least 0.007 inch, at least 0.008 inch, at least 0.009 inch, at least 0.010 inch, and the like.

Gap Structure

The following refers generally to gap ((28) in FIG. 2; (61) in FIG. 4), in non-limiting embodiments depicted in FIGS. 2 and 4. During insertion of dilator-sheath assembly into tissue, an axial load is applied to dilator from the tissue while the clinician holds the sheath body and applies the requisite opposite force. An elastic sheath body will stretch under this load causing a reduction of gap. In order to ensure that the sheath tip remains on the main shaft of the dilation member and does not advance over the radially enlarged region, potential stretch can be taken into consideration. In non-limiting embodiments, a 6 French extrusion undergoing a 5 lb load will undergo approximately 2% elongation. If sheath body was 5.0 inches in length at rest, the gap between the proximal edge of the radially enlarged dilation member and distal edge of the sheath tip is expected to be at least 0.10 inches and the gap for a 10.0 inch sheath is expected to be at least 0.20 inches.

Example Four

A non-limiting Verification Protocol for dilator tip and dilator/sheath tip transition insertion testing is as follows. Testing involves a Universal Test Machine (UTM), a 50N load cell, a test disc cutting block, a test disc steel rule die, a test pin (0.0185 inch diameter×4 inch long), a film (0.015 inch natural polyurethane (Stevens urethane ST-1880, Stevens Urethane, Easthampton, Mass.), and fixtures (transradial 4 Fr dilator/sheath holding; transradial 5 Fr dilator/sheath holding; transradial 6 Fr dilator/sheath holding; dilator test medium holding, and test disc centering).

Testing involves a "unit under test" (UUT), where the UUT is a tipped dilator extrusion inside a tipped sheath extrusion from a corresponding sheath introducer. The exposed length of the distal portion of the tipped dilator extrusion from the distal end of the tipped sheath extrusion can be adjusted prior to testing. Sample size per UUT group is 30 per FR (French) size.

Installation procedure involves attaching dilator test medium holding ficture to base of UTM and secure. Attaching 50N load cell to crosshead and secure. Plug the data input connector in the back of the crosshead and secure. Place the wire for the data input cord over the hook on the back of the crosshead so it does not interfere with vertical movement of the crosshead. Attach appropriate transradial sheath/dilator holding fixture with securing nut for the Fr size being tested into the load cell (hand tighten only). Regarding the test program, select dilator sheath penetration test. Verify insertion (crosshead) speed is 100 mm/min (4 in/min) on the test screen, and extension endpoint is as follows before beginning the procedure: 0.625 inch for assemblies; 1.625 inch for single taper dilators; 2.125 inch for double taper dilators. Select the upper and lower stops on the UTM to ensure personnel and equipment safety.

The following concerns preparation of test discs. Place test disc cutting block on the base of the Arbor Press (e.g., Northern Tool+Equipment, Burnsville, Minn.). Place the 0.015 inch polyurethane film to be cut on the cutting block. Place the test disc steel rule die onto the film in the area to be cut (sharp edge to film) and center under Arbor Press. Lower the Arbor Press arm to punch out the test disc. Do not apply excessive force to cause the cutting die blade to cut excessively into the cutting block. Raise the Arbor Press arm, and then remove the test disc steel rule die and test die. Move the film to an un-punched area and repeat above as required to create test discs for testing.

Regarding test samples, prepare test samples by inserting the dilator into the sheath maintaining 0.25 inch plus or minus 0.375 inch of exposed dilator tip beyond sheath tip. Ensure that the sheath tip is behind the proximal end of the dilator tip. Cut the overall length to 2.00 inch plus or minus 0.125 inch. For single taper dilators, insert the dilator into the sheath maintaining 1.25 inch plus or minus 0.25 inch of exposed dilator tip beyond sheath tip. Ensure that the sheath tip is behind the proximal end of the dilator tip. Cut the overall length to 3.00 inch plus or minus 0.125 inch. The cutting of the dilator and sheath extrusions allows them to fit and function in the test fixtures. The cutting does not affect the distal ends that are being tested. For double taper dilators, insert the dilator into the sheath, maintaining 1.625 inch plus or minus 0.125 inch of exposed dilator tip beyond the sheath tip. Ensure that the sheath tip is behind the proximal end of the dilator tip. Cut the overall length to 3.5 inch plus or minus 0.125 inch.

Regarding the procedure, the operational setup involved the following. Test medium is assembled by placing ten (10) prepared test discs into the base of the test disc centering fixture and then place the cap onto the base to secure the text discs. Insert a 21 gauge needle into a center hole on the cap, and push with a slight rotating motion until the hub of the needle is flush with the cap. While holding the cap and needle, remove them from the base, leaving the test discs on the needle. Carefully insert a test pin into the needle on the side having the test discs and slide a test disc onto the test pin.

The following is procedural testing steps. Ensure the installation procedure and operational setup are completed prior to starting the testing. For the dilator tip and dilator/sheath tip transition test, raise the handles on the dilator test medium holding fixture and remove the top. Place a test pin having a test disc into the dilator test medium holding fixture. Replace the top (align orientation indicators on top and base) and lower the handles on the dilator test medium holding fixture. Fully insert cut end of assembled dilator/sheath into the appropriate sized dilator/sheath holding fixture. Tighten handle screw to secure dilator/sheath in fixture. Zero the load cells. Slowly lower the crosshead while placing test pin in the dilator tip of the test sample. Continue to lower the crosshead until the dilator tip of the test sample is approximately 0.100 inch above the test disc, but not touching it. Then, zero the position of the crosshead. Hit the run test button. Select "OK" when the "crosshead about to return" screen appears. Return the crosshead to provide access to remove the test sample. Raise the handles on the dilator test medium holding fixture and remove the top. Remove the test sample from the fixture being careful not to bend the test pin. The test pin might have been pushed into the fixture and will require removal using tweezers. Remove test disc and discard. Remove and save the test pin for future use. The test discs cannot be reused.

The devices, methods, and characteristics of the present disclosure are not limited to a dilator-sheath assembly, but also encompass devices and methods of similar devices inserted through the skin to gain access to vasculature, including a sheath or catheter, or cannula, or into body cavities, such as a trocar.

While methods, devices, compositions, and the like, have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims. It is understood that the term, present disclosure, in the context of a description of a component, characteristic, or step, of one particular embodiment of the disclosure, does not imply or mean that all embodiments of the disclosure comprise that particular component, characteristic, or step.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC §132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible.

What is claimed is:

1. A dilator and sheath assembly, comprising:
    a sheath comprising an elongate tubular sheath body, the elongate tubular sheath body comprising a sheath proximal end and a sheath distal end, the elongate tubular sheath body having an inner body radius, the sheath distal end being circumferentially continuous and having an inner distal radius, and the sheath proximal end comprising a sheath hub defining an aperture; and
    a dilator comprising an elongate dilator shaft comprising a dilator proximal end and a dilator distal tip, and a dilator hub at the dilator proximal end, the dilator distal tip comprising a radially enlarged dilator bump, wherein:
    the dilator bump comprises a proximal taper that increases in radius from the proximal to distal direction, and a distal taper that decreases radius from the proximal to distal direction,
    the dilator bump has a maximum radius at a point between the proximal taper and the distal taper, the maximum radius of the dilator bump being greater than the inner distal radius of the sheath distal end, and
    the dilator bump is configured to pass through the elongate tubular sheath body by radially stretching at least the circumferentially continuous sheath distal end.

2. The dilator and sheath assembly of claim 1, wherein the sheath hub and the dilator hub are configured to be reversibly coupled.

3. The dilator and sheath assembly of claim 2, wherein, when the sheath hub and dilator hub are coupled, the proximal taper of the dilator bump is disposed entirely distal to the sheath distal end.

4. The dilator and sheath assembly of claim 2, wherein the dilator hub comprises a tongue and the sheath hub comprises a groove configured to receive the tongue of the dilator hub to reversibly couple the sheath hub and the dilator hub.

5. The dilator and sheath assembly of claim 4, wherein the groove of the sheath hub extends at least partially circumferentially around the sheath hub.

6. The dilator and sheath assembly of claim 1, further comprising a packaging that encloses said dilator and said sheath in a non-assembled state.

7. The dilator and sheath assembly of claim 1, wherein:
    the proximal taper of said dilator bump has a point of minimal radius, and
    when the dilator and sheath are assembled, a longitudinal gap between said point of minimal radius of the dilator bump and the sheath distal end has a gap length.

8. The dilator and sheath assembly of claim 7, wherein the gap length is:
    about 0.05 centimeters,
    at least 0.04 centimeters, or
    0.04-0.06 centimeters.

9. The dilator and sheath assembly of claim 1, wherein the dilator bump comprises a distal angle, a longitudinal axis, and an distal outer surface, the distal angle being defined between the distal outer surface and the longitudinal axis of dilator bump, and wherein the distal angle is about 0.03 degrees, about 0.07 degrees, or about 0.15 degrees.

10. The dilator and sheath assembly of claim 1, wherein the dilator bump comprises a proximal inner angle, a longitudinal axis, and an proximal inner surface, the proximal inner angle being defined between the proximal inner surface and the longitudinal axis of dilator bump, and wherein the proximal inner angle is about 0.022 degrees, about 0.078 degrees, or about 0.089 degrees.

11. The dilator and sheath assembly of claim 1, wherein, when the dilator and sheath are assembled:
    the elongate dilator shaft has an outer radius,
    the sheath defines a radially extending distance, and the maximum radius of the dilator bump is the sum of the outer radius of the elongate dilator shaft and about 50% of radially extending distance.

12. The and sheath assembly of claim 1, wherein, when the dilator and sheath are assembled:
   the elongate dilator shaft has an outer radius,
   the sheath defines a radially extending distance, and
   the maximum radius of the dilator bump is the sum of the outer radius of the elongate dilator shaft and about 75% of radially extending distance.

13. The dilator and sheath assembly of claim 1, wherein, when the dilator and sheath are assembled:
   the elongate dilator shaft has an outer radius,
   the sheath defines a radially extending distance, and
   the maximum radius of the dilator bump is the sum of the outer radius of the elongate dilator shaft and about 100% of radially extending distance.

14. The dilator and sheath assembly of claim 1, wherein, when the dilator and sheath are assembled:
   the elongate dilator shaft has an outer radius,
   the sheath defines a radially extending distance, and
   the maximum radius of the dilator bump is greater than the the outer radius of the elongate dilator shaft and about 100% of radially extending distance.

15. The dilator and sheath assembly of claim 1, wherein the sheath distal end is tapered, such that the inner distal radius of the sheath distal end is smaller than the inner body radius of said elongate tubular sheath body.

16. The dilator and sheath assembly of claim 1, wherein the sheath comprises a polytetramethylene glycol based polyurethane elastomer.

17. The dilator and sheath assembly of claim 1, wherein the dilator comprises a high density polyethylene resin.

18. The dilator and sheath assembly of claim 1, wherein, when the dilator and sheath are assembled, at least part of the sheath distal end overlaps with the proximal taper of the dilator bump.

19. The dilator and sheath assembly of claim 1, further comprising a lubricant between the elongate dilator shaft and the elongate tubular sheath body.

20. The dilator and sheath assembly of claim 19, wherein the lubricant comprises petrolatum or silicone.

* * * * *